(12) United States Patent
Echauz et al.

(10) Patent No.: US 7,333,851 B2
(45) Date of Patent: Feb. 19, 2008

(54) UNIFIED PROBABILISTIC FRAMEWORK FOR PREDICTING AND DETECTING SEIZURE ONSETS IN THE BRAIN AND MULTITHERAPEUTIC DEVICE

(75) Inventors: Javier Ramón Echauz, Atlanta, GA (US); Rosana Esteller, Marietta, GA (US); Brian Litt, Merion Station, PA (US); George John Vachtsevanos, Marietta, GA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 842 days.

(21) Appl. No.: 10/662,072

(22) Filed: Sep. 12, 2003

(65) Prior Publication Data
US 2004/0068199 A1    Apr. 8, 2004

Related U.S. Application Data

(63) Continuation of application No. 09/693,423, filed on Oct. 20, 2000, now Pat. No. 6,678,548.

(51) Int. Cl.
*A61B 5/04* (2006.01)
(52) U.S. Cl. ...................... 600/544; 608/378
(58) Field of Classification Search ............... 600/544, 600/545, 300, 378; *A61B 5/06, 5/04*
See application file for complete search history.

(56) References Cited

U.S. PATENT DOCUMENTS 3,837,331 A    9/1974 Ross .......................... 600/27

(Continued)

FOREIGN PATENT DOCUMENTS

GB    2336211 A    10/1999

OTHER PUBLICATIONS

Iasemidis, et al., "Spatiotemporal Evolution of Dynamical Measures Precedes Onset of Mesial Temporal Lobe Seizures," *Epilepsia*, vol. 35, No. Suppl. 8, pp. 133, 1994.

(Continued)

*Primary Examiner*—Daniel Robinson
(74) *Attorney, Agent, or Firm*—Womble Carlyle Sandridge & Rice

(57) ABSTRACT

A method and an apparatus for predicting and detecting epileptic seizure onsets within a unified multiresolution probabilistic framework, enabling a portion of the device to automatically deliver a progression of multiple therapies, ranging from benign to aggressive as the probabilities of seizure warrant. Based on novel computational intelligence algorithms, a realistic posterior probability function $P(S_T|x)$ representing the probability of one or more seizures starting within the next T minutes, given observations x derived from IEEG or other signals, is periodically synthesized for a plurality of prediction time horizons. When coupled with optimally determined thresholds for alarm or therapy activation, probabilities defined in this manner provide anticipatory time-localization of events in a synergistic logarithmic-like array of time resolutions, thus effectively circumventing the performance vs. prediction-horizon tradeoff of single-resolution systems. The longer and shorter prediction time scales are made to correspond to benign and aggressive therapies respectively. The imminence of seizure events serves to modulate the dosage and other parameters of treatment during open-loop or feedback control of seizures once activation is triggered. Fast seizure onset detection is unified within the framework as a degenerate form of prediction at the shortest, or even negative, time horizon. The device is required to learn in order to find the probabilistic prediction and control strategies that will increase the patient's quality of life over time. A quality-of-life index (QOLI) is used as an overall guide in the optimization of patient-specific signal features, the multitherapy activation decision logic, and to document if patients are actually improving.

18 Claims, 4 Drawing Sheets

U.S. PATENT DOCUMENTS

| | | | |
|---|---|---|---|
| 3,850,161 A | 11/1974 | Liss | 600/544 |
| 3,863,625 A | 2/1975 | Viglione et al. | 128/2.1 |
| 3,967,616 A | 7/1976 | Ross | 600/27 |
| 3,993,046 A | 11/1976 | Fernandez et al. | 600/545 |
| 4,566,464 A | 1/1986 | Piccone et al. | 600/545 |
| 4,702,254 A | 10/1987 | Zabara | 607/45 |
| 4,735,204 A | 4/1988 | Sussman et al. | |
| 4,867,164 A | 9/1989 | Zabara | 607/45 |
| 5,025,807 A | 6/1991 | Zabara | 607/45 |
| 5,304,206 A | 4/1994 | Baker, Jr. et al. | 607/2 |
| 5,311,876 A | 5/1994 | Olsen et al. | 600/544 |
| 5,713,923 A | 2/1998 | Ward et al. | 607/3 |
| 5,743,860 A | 4/1998 | Hively et al. | 600/544 |
| 5,857,978 A | 1/1999 | Hively et al. | 600/544 |
| 5,928,272 A | 7/1999 | Adkins et al. | 607/45 |
| 5,978,702 A | 11/1999 | Ward et al. | 607/3 |
| 5,995,868 A | 11/1999 | Dorfmeister et al. | 600/544 |
| 6,016,449 A | 1/2000 | Fischell et al. | 607/45 |
| 6,018,682 A | 1/2000 | Rise | 607/45 |
| 6,061,593 A | 5/2000 | Fischell et al. | 600/544 |
| 6,678,548 B1 * | 1/2004 | Echauz et al. | 600/544 |
| 2004/0068199 A1 * | 4/2004 | Echauz et al. | 600/544 |
| 2004/0152958 A1 * | 8/2004 | Frei et al. | 600/300 |

OTHER PUBLICATIONS

Iasemidis, et al.,"Chaos Theory and Epilepsy", *The Neuroscientist*, Mar. 1996, vol. 2, No. 2, pp. 118-126.

Grassberger, et al. "Characterization of Strange Attractors," *Physical Rev. Letters*, vol. 50, No. 5, pp. 346-349.

Elger, et al., "Seizure Prediction by Nonlinear Time Series Analysis of Brain Electrical Activity," *European Journal of Neuroscience*, 1998, vol. 10, pp. 786-789.

\* cited by examiner

UNIFIED PROBABILISTIC FRAMEWORK FOR PREDICTING AND DETECTING SEIZURE ONSETS IN THE BRAIN AND MULTITHERAPEUTIC DEVICE

CROSS-REFERENCE TO RELATED APPLICATIONS

This application is a division of application Ser. No. 09/693,423, filed Oct. 20, 2000, now U.S. Pat. No. 6,678,548.

This application is related to co-pending patent application "Adaptive Method and Apparatus for Forecasting and Controlling Neurological Disturbances Under a Multi-Level Control", Ser. No. 09/693,423, having the same inventorship. The present application is also related to international application WO 00/10455, published under the Patent Cooperation Treaty (PCT) on Mar. 2, 2000. The related patent applications are hereby incorporated by reference into this description as fully as if here represented in full.

BACKGROUND OF THE INVENTION

The present invention is in the field of medical devices to treat neurological disorders of the brain. More specifically, the invention is directed to a method and a partially or fully implanted apparatus for predicting and detecting epileptic seizure onsets within a unified multiresolution probabilistic framework, thereby enabling a portion of the device to automatically deliver a progression of multiple therapies, ranging from benign to aggressive as the probabilities of seizure warrant, in order to deter the course of a seizure with only the minimally required intervention and associated side effects.

Second to stroke, epilepsy is the most common neurological disorder of the brain. It is characterized by recurrent seizures that significantly impair the quality of life of an estimated 1 to 2% of the world's population. Drugs are the most common form of treatment, but their efficacy is limited. Up to 30% of patients achieve no control of their seizures with drugs, and another 30% experience severe side effects that make it impossible to lead normal lives.

A personal device capable of warning and/or intervening therapeutically in response to imminent seizures would allow those with epilepsy to, at a minimum remove themselves from danger (e.g., stop driving a car), and in the best case become seizure-free, not even noticing times when they were about to have a seizure. Such a device would operate in a continuous-time closed control loop where therapy is responsive to measurements (this includes a patient's own actions in the loop).

Several prior art closed-loop responsive systems with applicability to improving the quality of life of epileptic individuals are known to have been proposed in the field to date. All prior art systems share the following disadvantages: (1) they only detect visually obvious changes in raw signals thus control of seizures is attempted only after individuals actually begin having each seizure; (2) they implement a deterministic approach which is inadequate in face of the uncertainty and complexity of the problem; (3) they offer no means of gauging confidence in the outputs; (4) they implicitly assume a single (infinite) time resolution which may be adequate for seizure detection but not prediction; (5) they suggest a control scheme which is closed-loop only at the triggering instant dictated by detection (treatment beyond that point is open-loop, and is called triggered open-loop control in the present invention); (6) they do not deliver therapy that is graded from benign to aggressive as the situation warrants; (7) they do not consider side effects; (8) they imply detection schemes that are not guided by optimality criteria; (9) they rely on a single input feature or multiple features of the same nature (e.g., power in frequency bands) or only few uncorrelated features; (10) they use the same features for the whole patient population and do not take advantage of patient-specific features; (11) they do not transfer adequate samples of data for offline analysis; (12) they possess little or no computational intelligence with no learning capabilities to automatically improve and maintain performance over time; (13) they directly threshold separate single features instead of an implicit likelihood ratio function of joint features thereby yielding suboptimal decision rules; and (14) they do not account for the fact that training and/or testing seizure detectors/predictors with wrong prior probabilities of seizures/preseizures (as reflected in raw data archives or clinical trials) induces a variety of distortions that must be corrected.

The present invention is directed to overcome the disadvantages and limitations of all prior art.

SUMMARY OF THE INVENTION

The invention is directed to a method and a partially or fully implanted apparatus for predicting and detecting epileptic seizure onsets within a unified multiresolution probabilistic framework, thereby enabling a portion of the device to automatically deliver a progression of multiple therapies, ranging from benign to aggressive as the probabilities of seizure warrant, in order to prevent, abort, or mitigate the intensity, duration, frequency, and spread of seizures with only the minimally required intervention and associated side effects. Based on novel computational intelligence algorithms, a realistic posterior probability fuinction $P(S_T|x)$ representing the probability of one or more seizures starting within the next T minutes, given observations x derived from intracranial EEG (IEEG) or other signals, is periodically synthesized for a plurality of prediction time horizons (scales T, or resolutions 1/T), e.g., a second, a minute, ten minutes, an hour, etc. When coupled with optimally determined thresholds for alarm or therapy activation, probabilities defined in this fashion provide anticipatory time-localization of events in a synergistic logarithmic-like array of time resolutions, thus effectively circumventing the performance vs. prediction-horizon tradeoff of single-resolution systems. For example, whereas it is unrealistic to predict the exact onset time of a seizure as 9 minutes and 58 seconds from now, it is both realistic and useful to predict that the onset will occur anytime within the next 10 minutes, a time during which the seizure can be prevented using a benign form of treatment. The longer and shorter prediction time scales are made to correspond to benign and aggressive therapies respectively. In addition to providing degrees of confidence and fine monitoring of patients' states, probabilities can be advantageously treated as degrees of "imminence" of events. Such degrees in turn serve to modulate the dosage and other parameters of treatment during open-loop or feedback control of preseizures once activation is triggered. Fast seizure onset detection is unified within the framework as a degenerate form of prediction at the shortest, or even negative, time horizon. The device is required to learn in order to find the probabilistic prediction and control strategies that will increase the patient's quality of life over time. A quality-of-life index (QOLI) is used as an overall guide in the optimization of patient-specific signal features, the multitherapy activation decision logic, and to document if patients are actually improving.

A distinguishing theme of the present invention is that prediction is achieved for most patients and circumstances well before electrographic onset of seizures, and before any changes in raw physiologic signals that are visually obvious to a human expert. These prediction windows afford sufficient time to discourage seizures starting with mild forms of treatment, and escalating into multitherapeutic regimes only as it becomes necessary. Therefore, a principal objective of the invention is to avert seizures in the brain using only the minimally required interventions and their attendant side effects.

The present invention exploits the synergy of multiple signal features of a different nature. Features are accessed from a rich feature library including instantaneous, historical, spatial, and artificial features. Patient-specific signal features are exploited. Conventional features are custom-searched, and artificial features are custom-made, for each patient and prediction horizon, optimizing prediction performance and computational requirements. The invention exploits the synergy of multiple time resolutions in parallel.

The invention displays probabilities of oncoming seizures, each associated with a prediction horizon/resolution, in order to indicate both the time frame when onsets are expected to occur, and degrees of confidence in the predictions.

The value of the probabilities can be deliberately influenced by using them as controlled variables in a hierarchical seizure controller consisting of multitherapy activation decision logic and triggered open-loop or feedback control laws/actuators.

Multitherapy activation decisions can be based on user-selectable classifier-based optimality criteria (e.g., minimum error, minimum error risk, minimum overall risk, minimum false positives subject to constant false negatives, etc.), all in turn directed to maximize QOLI. The invention unifies seizure onset detection as a degenerate form of prediction at the finest time resolutions.

Because therapies can change the very patterns that the device is designed to initially recognize, a seizure predictor-controller (or seizure onset detector-controller), must have learning capabilities, otherwise it is only a matter of days before it becomes ineffective. It is therefore a further principal objective of the invention to teach novel computational intelligence learning algorithms required for a device to improve and maintain its performance over time. Such methods include the ability to correct for mismatches between the prior probability of preseizures/seizures that is incorrectly inferred from training data, and the patient's real-life probabilities of those events.

The above and other novel features, objects, and advantages of the invention will be understood by any person skilled in the art when reference is made to the following description of the preferred embodiments, taken in conjunction with the accompanying drawings.

DETAILED DESCRIPTION OF THE INVENTION

The present invention is directed to a method and an apparatus for predicting and detecting the onset of seizure disorders within a unified, multiresolution probabilistic framework that enables a portion of the apparatus to deliver automatically a progression of multiple therapies. The therapies range from benign to aggressive as the probabilities of seizure warrant, in order to prevent, abort or mitigate the intensity, duration, frequency and spread of seizures.

Figure 1:
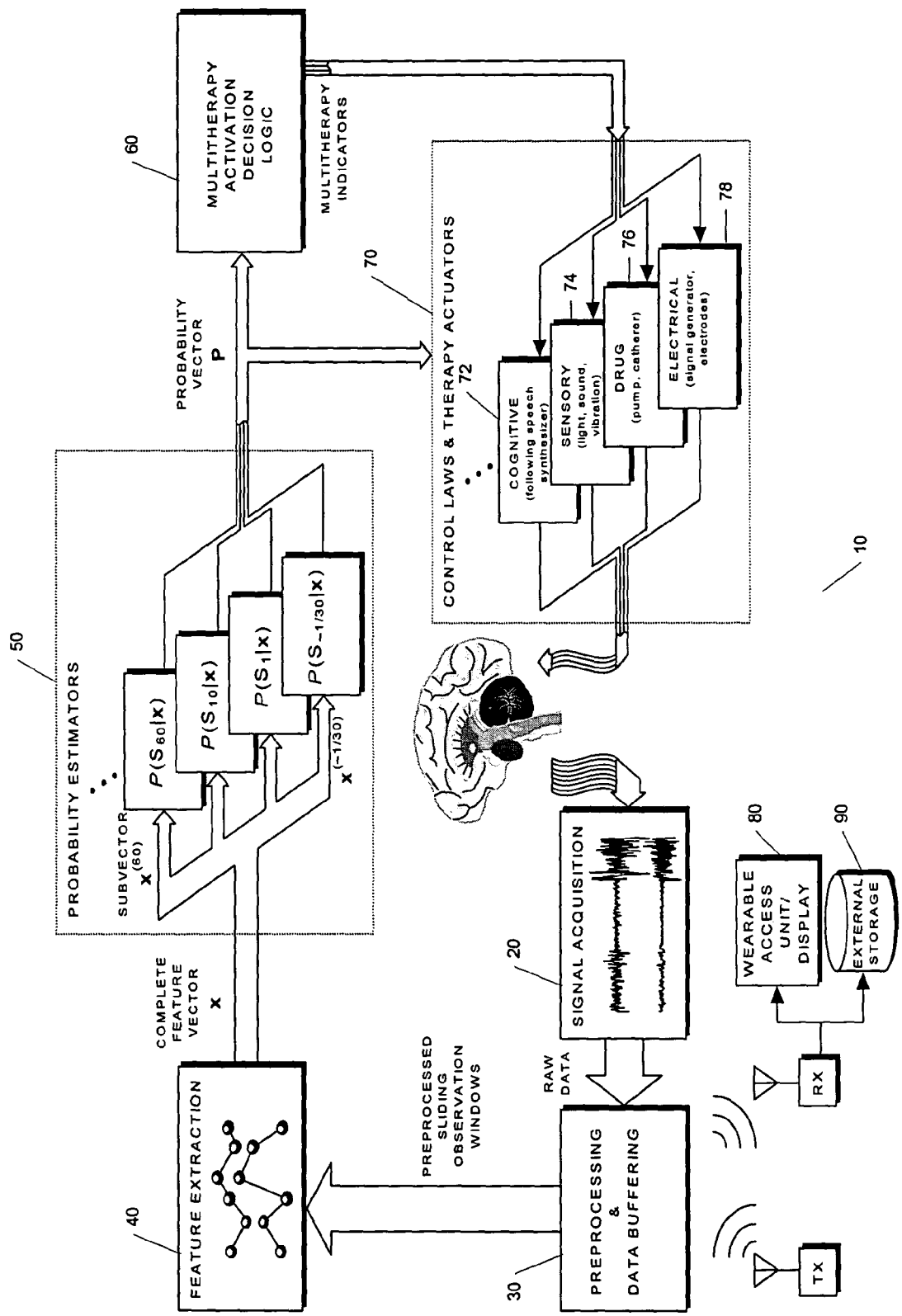
FIG. 1 illustrates a functional block diagram of the system in online operation mode.

FIG. 1 illustrates an exemplary architecture of a seizure prediction and control system 10 in an online operation mode, according to the present invention. A signal acquisition portion 20 conditions (amplifies, filters, isolates, multiplexes, etc.), and digitizes multiple raw signals, preferably intracranial EEG (IEEG). The acquired multichannel data are preprocessed 30 to attenuate artifacts such as any residual 60 Hz contamination, bad transducer contact, etc. Other steps that may be associated with preprocessing in some cases but not universally, are considered to be part of the feature extraction algorithms. Examples of these include: bipolar derivation of two referential signals, and recurrent standardization of signal amplitudes based on exponentially weighted moving averages (EWMA) of the mean and standard deviation of those amplitudes. The buffer in this portion implements a sliding observation window of present and past data used by the feature extraction algorithms, typically spanning periods of 1 to 10 times the prediction horizon T. Data subsampling allows the buffer size to remain fixed.

The feature extraction portion 40 contains selectable algorithms and mathematical formulas that distill relevant seizure-predictive and seizure-indicative attributes from the high-dimensional preprocessed signals. Multichannel data within the sliding observation window (typically 400 to hundreds of thousands of numbers) are converted into a low dimensional vector $[x_1\ x_2\ \ldots\ x_n]$ containing 10 or less features for each time scale (usually 40 or less numbers in the complete vector). Features can be any linear or nonlinear projection of raw data into another space, including the same raw data without compression as a special case. Features can be updated as fast as the raw data sampling rate (e.g., 200 Hz), but typically the fastest feature sampling is set as one every 0.45 seconds. Longer-horizon features can be updated less frequently according to a no-less-than-50% sliding window overlap criterion. Distinctly from all the prior art contemplating features, the feature vector is made patient-specific and optimized from a rich feature library of instantaneous, historical, spatial, and artificial features. An exemplary feature library is disclosed in co-pending application Ser. No. (Attorney Docket I080 1020). Examples of useful features include accumulated energy profiles, quick fractal dimension (curvelength), absolute values of wavelet coefficients, nonlinear energy, spectral entropy, prodrome templates, the statistical moments of any feature, and custom-made genetically found, neurally computed features.

The complete feature vector x is demultiplexed into constituent subvectors each corresponding to a particular time scale: $x = [x^{(60)}\ x^{(10)}\ x^{(1)}\ x^{(-1/30)}]$ (for brevity, time scale superscripts will be dropped hereinafter). Equivalently, the feature extraction portion 40 can be implemented as subsystems that individually compute feature vectors from different observation windows. Each probability estimator P($S_T$|x), implemented by a wavelet neural network or any other universal approximator, draws from its recent collective knowledge regarding the behavior of its feature vector x in order to compute the probability that one or more seizures will begin at any time within the next T minutes. In FIG. 1, T is shown for 60, 10, 1, and −1/30 minutes. The latter defines a seizure onset detector within the first 2 seconds of electrographic seizure. The horizon T should not extend beyond about one fourth (¼) of the average inter-seizure period (e.g., if a patient is known to have one seizure a day, then it is not informative to predict a seizure within the next day, or week, or year, etc., but it becomes increasingly useful within the next 6 hours and less). Instead of a single-resolution system attempting to determine the exact time remaining to seizure after a precursor occurs, the synergistic logarithmic-like array of time resolutions is used to cover a wide range of time frames when precursors may occur. This, in conjunction with the way in which the $S_T$ event is defined, effectively circumvents the performance vs. prediction-horizon tradeoff of single-resolution systems.

The posterior probability provides information beyond the prior probability of preseizures, P($S_T$), to the extent that the feature vector x behaves differently under preseizure and nonpreseizure conditions. For example, if the statistical behavior of x is identical under the two classes (including seizures and nonseizures as degenerate special cases), then P($S_T$|x)=P($S_T$), intelligent time-localization of events would not be possible using those features, and the device would operate in sensorless, purely open-loop mode. It should be noted that equal distributions do not imply that x is not useful; a dynamic feature of x may well be separable, but that is a new and different x. It is well known that EEG features are vastly different under seizure and nonseizure conditions, to the extreme of visual obviousness in the raw signals, so that automatic seizure detection with very high reliability is straightforward. Research to date has also shown that there exists premonitory features, most often in raw signals invisible to the naked eye, that enable preseizure detection with degrees of certainty ranging from moderate to very high. An important additional consideration for a feature to be discriminatory is that its variances under each class be relatively small. If a feature x varies wildly at every feature sampling time, so will the probability P($S_T$|x). This is simply a reflection of the fact that the feature is an inconsistent correlate of the classes. Integrating a series of "preprobabilities," as in sequential hypothesis testing, and taking that as a new input feature, or calculating moving averages or standard deviation charts of features, are all examples of making features more historical in nature so as to stabilize their behavior and thus their utility to the probability function.

The probability estimation portion 50 outputs a probability vector P=[$P_{60}$ $P_{10}$ $P_1$ $P_{-1/30}$], which is then taken as input to a hierarchical multiple-input-multiple-output seizure controller 70. The multitherapy activation decision logic block 60 determines which therapy modalities (control laws and therapy actuators 70) are activated or deactivated at any given time. Therapies can include cognitive stimulation 72 (with speech synthesizer that reads out an arithmetic or other mental task), sensory stimulation 74 (audio, visual, tactile, olfactory, kinesthetic, or other), biofeedback, electrical stimulation 78, pharmacological infusion 76, or other. For each therapy modality that is activated, a control law u=g(P) defines exactly how that therapy actuates on the brain. In triggered open-loop mode, fixed parameters such as drug dosage, or amplitude, frequency, pulse width, phase, etc., of preprogrammed electrical stimulation waveforms are obtained by considering the probability vector only at the time of activation: u=g(P(x($t_a$))). More generally, in feedback control mode 70, the control action is a function of the continuously varying probability vector: u(t)=g(P(x(t))). In this case, proportional, proportional-integral-derivative (PID), optimal continuous, gain-scheduled, multilevel, bang-bang, or other control strategies are envisioned in order to regulate P(x(t)), as a controlled variable, back to the zero vector [0000]. That is, intervention is automatically continuously modified so as to steer neural activity away from conditions known to be consistent with the future occurrence of seizures. Feedback control 70 offers the most finely graded form of treatment and potential for absolutely minimal intervention and the attendant side effects, however, obtaining stable closed-loop controls requires more extensive experimentation during presurgical evaluation than the triggered open-loop alternative. The device can also be programmed to work in purely open-loop mode (delivering prophylactic treatment at preset on and off times), and can be manually operated by the patient via a button, magnet, vibration transducer, or any other switching technique.

The device transmits its internally buffered data and other variables around the times of all therapy activations, as well as at a random or a preprogrammed sampling of times, including all times, by well known radiotelemetry. The probability vector P and multitherapy activation status are displayed in the patient's wearable access unit 80. The steps of preprocessing 30, feature extraction 40, probability estimation 50, and multitherapy decision logic 60 can be implemented in a microprocessor, a digital signal processor (DSP), a field programmable gate array (FPGA), an application specific integrated circuit (ASIC), hybrid analog/digital circuitry, or combinations thereof following design principles well known in the microelectronics industry.

This intelligence structure is coupled to an array of interventions based upon electrical stimulation, chemical infusion and synthesis of artificial neuronal signals to counteract developing seizures as precursors build over time. The intensity of intervention, modality of therapy and spatial distribution of therapy are all adjusted as the probability of seizures increases over time. A guiding principle of these interventions is that the most benign forms of therapy are initiated relatively early in seizure generation and over a relatively small region of the brain, so as to cause little or minimal disruption of normal activity when the probability of seizure onset is relatively low. This will allow intervention to be triggered by prediction thresholds with high sensitivity (e.g., very low false negative rate) at the cost of a relatively low specificity (e.g., relatively high false positive rate). As the probability of seizures increases, therapeutic stimuli are increased in intensity, duration, frequency of delivery, and are delivered over a wider area of the brain. Since patterns of seizure precursors and their spread in space and time leading up to seizures are mapped and used to train the device on each individual patient, therapy is delivered over broader areas, just ahead of the anticipated region of spread, as seizure precursors develop, if they do not respond to earlier treatment. In this scheme, therapy can be delivered locally, in the region of onset, in a distribution surrounding the region of onset, isolating it from recruiting adjacent regions of the brain and spreading. Therapy can also be delivered locally and/or remotely in subcortical regions such as the thalamus, basal ganglia, or other deep nuclei and regions, escalating in intensity, type of stimulus and distribution of action, as seizures progress. This same principle is applied to therapeutic intervention if electrical seizure onset takes place, effecting treatment in the general region of onset, in deep brain structures which modulate the behavior of the seizure focus, or both simultaneously.

Interventions can include the following: (1) rhythmic electrical pacing, which changes in frequency, intensity and distribution as the probability of seizure onset reaches a threshold and increases; (2) chaos control pacing; (3) random electrical stimulation to interfere with developing coherence in activity in the region of and surrounding the epileptic focus; and (4) depolarization or hyperpolarization stimuli to silence or suppress activity in actively discharging regions or regions at risk for seizure spread. This activity can also be delivered to numerous electrode sites to create a type of "surround inhibition" to prevent progression of seizure precursors. These stimuli can also be delivered sequentially in a "wave" that sweeps over a region of tissue, so as to progressively inhibit normal or pathological neuronal function in a given region(s) or tissue, including cortical and subcortical regions.

The principle of altering and developing therapy in response to the changing probability of seizure, and/or the detection of specific events in seizure evolution, including electrical seizure onset and spread, is also applied to the delivery of chemical therapy. In this fashion, active therapeutic agents are infused or otherwise released in the brain regions where seizures are generated, or to where seizures may spread. As seizures become more likely, the amount, concentration or spatial distribution through which a chemical agent is delivered are all increased. As with electrical or other therapeutic interventions, patterns of delivery can include infusing a drug directly in the epileptic focus, in an area surrounding it, or to regions involved in early spread, or to more central or deep brain regions, which may modulate seizure propagation. These same therapeutic principles apply to distribution of maximal therapy when electrical seizure onset is detected, including distributing therapy to regions where seizures are known to spread and propagate. Last-minute treatment may include release of larger amounts of drug into the cerebrospinal fluid (CSF) space for circulation over wide regions of the brain or into the cerebral circulation. Other types of pharmacological agents may also be used in this scheme, such as agents which are activated by oxidative stress, which may themselves increase the concentration and distribution of an active therapeutic agent as seizure precursors evolve and the probability of seizures increases.

Therapy may also include delivery of stimuli, electrical, chemical or other, to peripheral or central nerves or blood vessels, in a graded fashion, as the probability of seizures increases, building up to therapy of maximal intensity at the detection of electrical seizure onset. Therapy may also include sensory stimulation (touch, temperature, visual, auditory etc.).

Finally, therapy may consist of synthesized, artificial neuronal signals delivered in such a way as to disrupt electrochemical traffic on the appropriate neuronal networks including or communicating with the ictal onset zone. Examples of such interventions might include transmission of synthesized signals which increase the output of specific cell populations, such as inhibitory interneurons, specific nuclear regions in the thalamus or other deep structures.

Using any or all of these methods singly, or in combination, therapy is directed toward preventing seizure onset, or isolating the development of seizures and their propagation so as to prevent or minimize clinical symptoms and the impact of these events.

Figure 2:
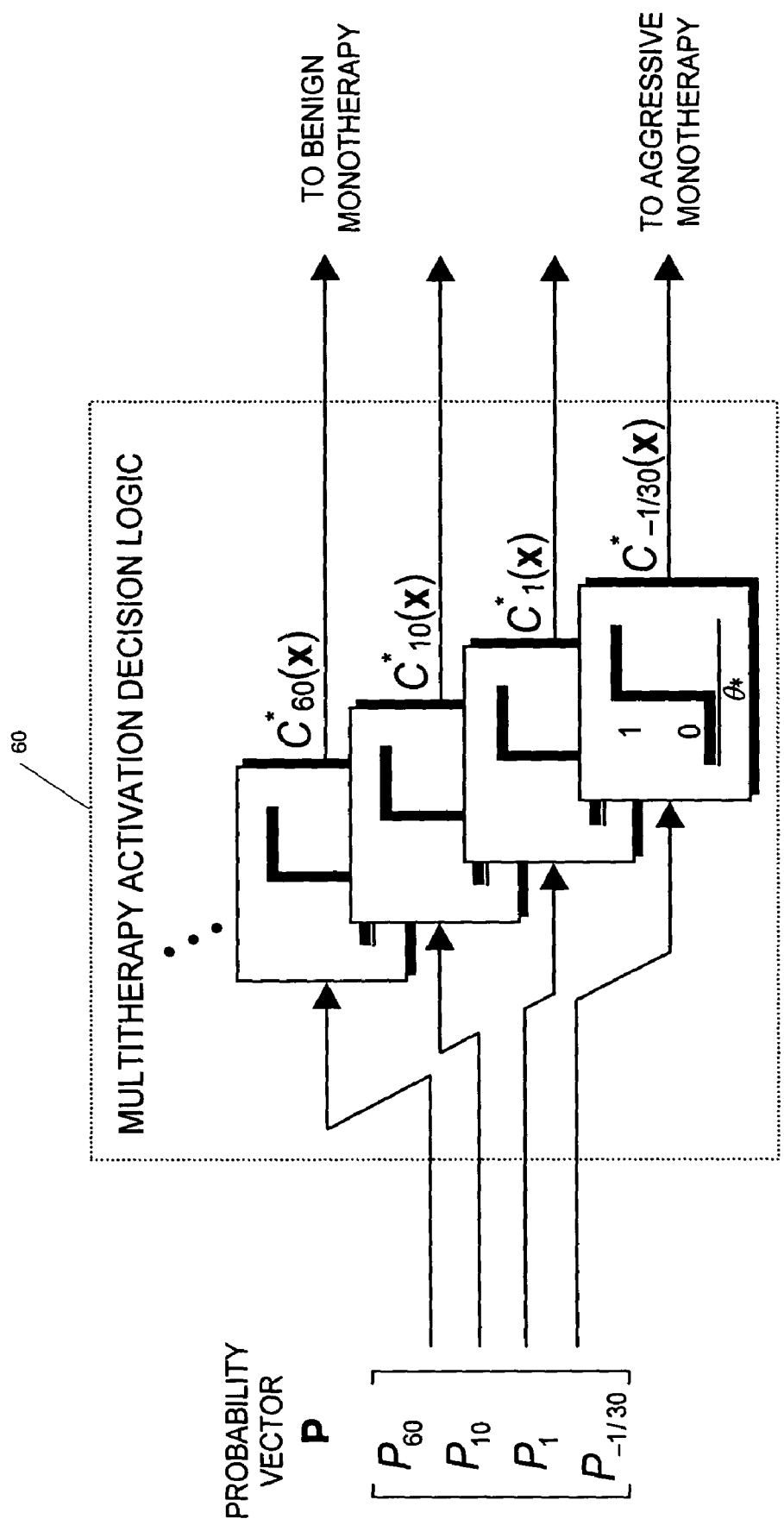
FIG. 2 illustrates an exemplary multitherapy activation decision logic.

FIG. 2 shows an example of a simple, yet very effective decision logic for multitherapy activation. The multivariable relation between probabilities and therapies is decoupled by tying each therapy mode to a particular prediction horizon: benign monotherapy to a large scale (coarse resolution), and aggressive monotherapy to a small scale (fine resolution). This is based on the principle, borne out of research, that the earlier the course of a seizure is interrupted, the more likely it is for a mild form of treatment to be successful. Therefore, as in the exemplary decision logic, benign treatment is encouraged first in order to reach the point of minimally invasive but sufficient therapy. Each subsystem will be independently activated based upon its own $P(S_T|x)$, sometimes simultaneously if such control force becomes necessary. As will be further disclosed hereinafter, this scheme makes it possible to learn each $P(S_T|x)$ using simple classifier-based optimality criteria. It also allows the seizure controller in the device to remain off most of the times, consuming only the minimum power necessary to avert seizures.

The following simplified example serves to illustrate a worst-case scenario of the inventive system in online triggered open-loop mode as a seizure approaches, but is not intended to preclude other ways in which the system could have behaved or could have been practiced. The probability vector for the next month in a patient's device is determined to be $P=[P(S_{60}|x_1) \ P(S_{10}|[x_2 \ x_3]) \ P(S_1|x_4) \ P(S_{-1/30}|x_5)]$, where $x_1$=60-minute resetting energy buildup at a focal channel, $x_2$=exponentially weighted moving average (EWMA) of signal power 98% forgotten after 10 minutes renormalized by last hour reference, $x_3$=count of 1-minute standard deviation excursions above a threshold over the last 10 minutes, $x_4$=1-minute moving average of nonlinear energy, and $x_5$=½ second signal curvelength. Two hours before (i.e., time −120 min.) the electrographic onset (time zero) of a particular seizure, the P values are hovering close to zero. Since the prior probabilities of preseizure-class features are very small for the chosen prediction time scales, the posterior P values will also tend to remain close to zero unless really unique feature changes are observed. At time −40 min., $P=[0.65 \ 0.1 \ 0.2 \ 10^{-4}]$. Note that the P values are not necessarily monotonically related (e.g., $P_1$ "more likely" than $P_{10}$) because the estimators are different mathematical functions trained to examine different features over the different time scales. In fact, if such monotonicity always held true, then the synergistic multiresolution advantage of the invention would be lost. The value $P_{60}$ already reached a threshold that triggers an audio waveform with preprogrammed characteristics. Note that a 60-minute prediction horizon does not imply that activation will happen exactly at $t_a$=−60 min., though earlier activation does imply an error ($P_{60}$'s job is to time-localize within a specific 60-minute time frame, not predict at "random" times). It is 3:00 am and the patient is awakened by the device, but through the wearable access unit 80, he or she may choose to block out this type of treatment during programmed times of the day, or a sleep state detector may do so automatically. Within a minute, $P_{60}$ falls below its activation threshold and stimulation shuts down, however at time −12 min. it goes back up, and at −8 min., $P_{10}$ also exceeds its threshold and a speech synthesizer temporarily disables audio stimulation while it asks the patient to carry out a mental calculation. The patient does so while simultaneous audio stimulation takes place. Despite these efforts to discourage seizure-inducing synchronized neural activity, $P_1$ indicates at time −30 sec. that the seizure is imminent, and electrical stimulation directly to the brain or to nerves under the skin is initiated. At one second past electrographic onset, still before any clinical symptoms, $P_{-1/30}$ reaches 0.95 and a drug is released directly to the brain or through the spinal cord. If the probability estimators were not trained including time segments of seizures under treatment, then they are temporarily disabled at this point (but not their associated therapies). Within a few more seconds, all traces of seizure have subsided and the seizure controller 70 is shut down. The skilled practitioner will recognize that progressive multitherapy as in the present invention is gentle enough to exhaust the possibilities of milder and safer forms of intervention first, but tough enough to ensure that a seizure will never go past treatment into its full expression.

In a close variation of the treatment decision logic of FIG. 2, two or more duplicate time scales can be used to activate the same therapy modality but differing only in treatment parameters, based on mutually exclusive intervals of P (instead of a threshold). For example, a small dosage may be used if $0.7 \leq P < 0.8$, a moderate one if $0.8 \leq P < 0.9$, and a strong one if $P \geq 0.9$. The actual values of the thresholds can be much smaller for small time scales T as will become apparent from subsequent description of the methods.

A system aimed to reduce or eliminate seizures, such as the present invention, must have interventive capabilities, otherwise it would only detect or predict seizures silently and without affecting the brain. If there is intervention, then the observable behavior of seizures changes over time (consider for example decreased seizure frequency, effects of kindling, or the difference between EEG data with and without drug tapering). If the patterns of seizures change over time, then the device must have learning capabilities, otherwise it will be only a matter of days before the system becomes ineffective. Therefore, advantageously over all prior art, the present invention conceives and discloses computational intelligence learning algorithms necessary to improve and maintain the device effectiveness over time.

Figure 3:
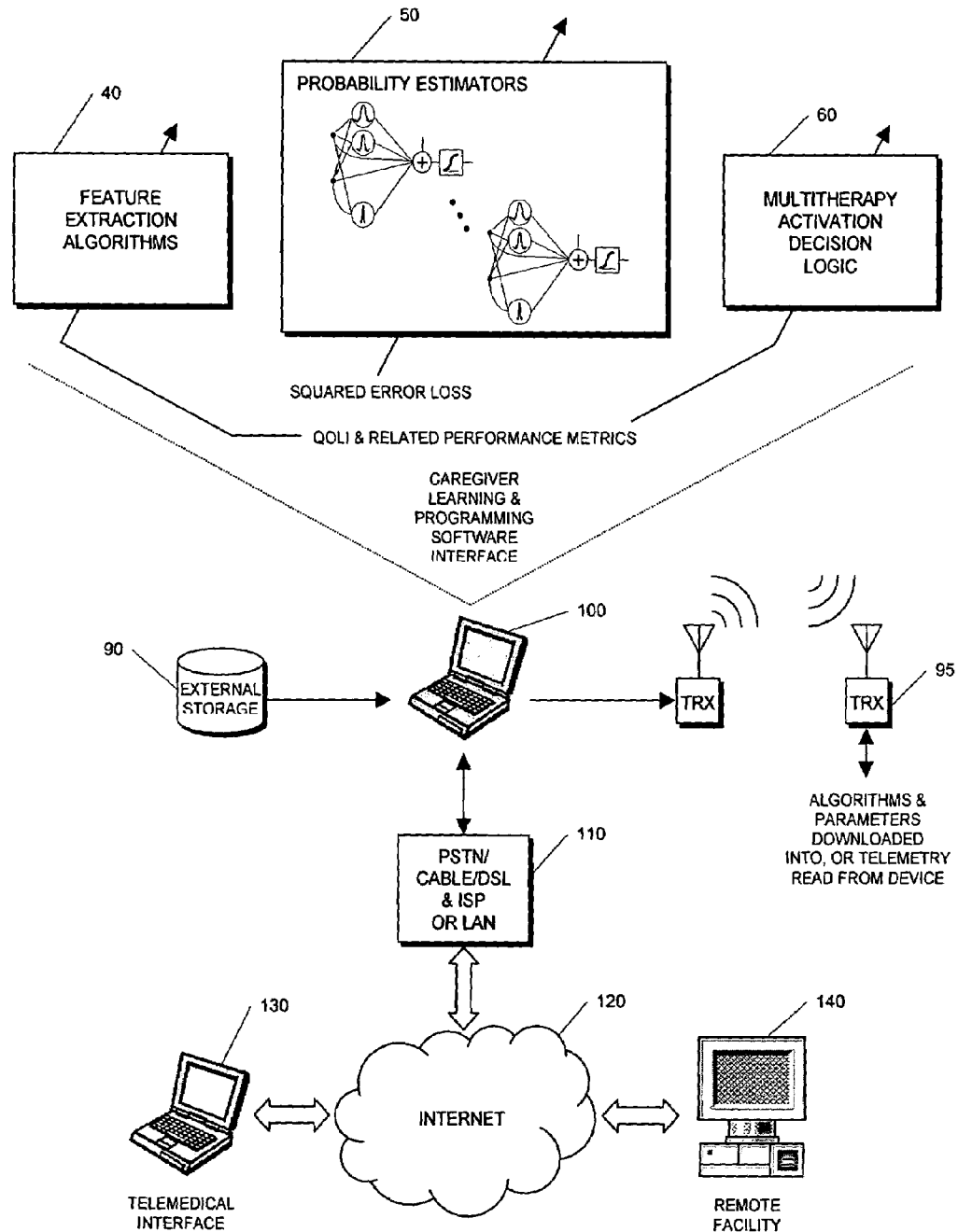
FIG. 3 illustrates a functional block diagram of the system in learning and programming mode.

FIG. 3 is an exemplary functional block diagram of the seizure predictor-controller system in learning and programming mode. During preoperative evaluation and periodically thereafter, typically once every month, an authorized caregiver is able to access the past period's data from the external storage device 90, train the feature extraction 40, probability estimation 50, and multitherapy activation decision logic 60 portions of the patient's device for optimum performance over the next period, download the learned algorithms and parameters into the device's electronically erasable programmable read-only memory (EEPROM) via transceivers 95, program other device settings, and telemeter the device settings and operating variables at any time, including during online mode, all through a centralized learning and programming software interface. The laptop or workstation computer 100 where this software runs can faithfully simulate the actions of the feature extraction 40, probability estimation 50, and multitherapy activation decision logic 60 portions of the device, and more importantly, can learn how to alter those portions in order to bring about performance improvement and maintenance. The ability of the system to carry out this function externally is crucial, since the required learning algorithms are CPU-time and memory expensive. "Learning" within the implanted device itself under severe clock speed, memory, and power constraints necessarily involves depriving the device of most of its potential intelligence. The learning and programming functions can also be carried out regardless of the patient's or caregiver's physical locations. A connection is established through the public switched telephone network, cable network, or digital subscriber line, and a service provider, or through local area network, collectively 110, then via a T1 line or other high speed digital link to the Internet 120, all the way to the remote caregiver's portable computer 130 or to a remote facility 140 where the same software interface runs.

The first training of the system can be based on IEEG data archived during routine preoperative evaluation, usually over a period of three to fourteen days. An optional bedside version of the device can be used during this period prior to transferring the initial algorithms and parameters into the partially or fully implanted device. The bedside unit can be built by implementing signal acquisition 20, preprocessing 30, feature extraction 40, probability estimation 50, and activation decision logic 60 within the laptop computer or workstation 100 that runs the programming and learning software interface, and a set of external therapy actuators. In some cases where a target location of electrodes is not well defined, especially in patients with generalized seizures, the archival during presurgical evaluation step can be obviated and the device can be implanted untrained to serve as the data collector itself.

Figure 4:
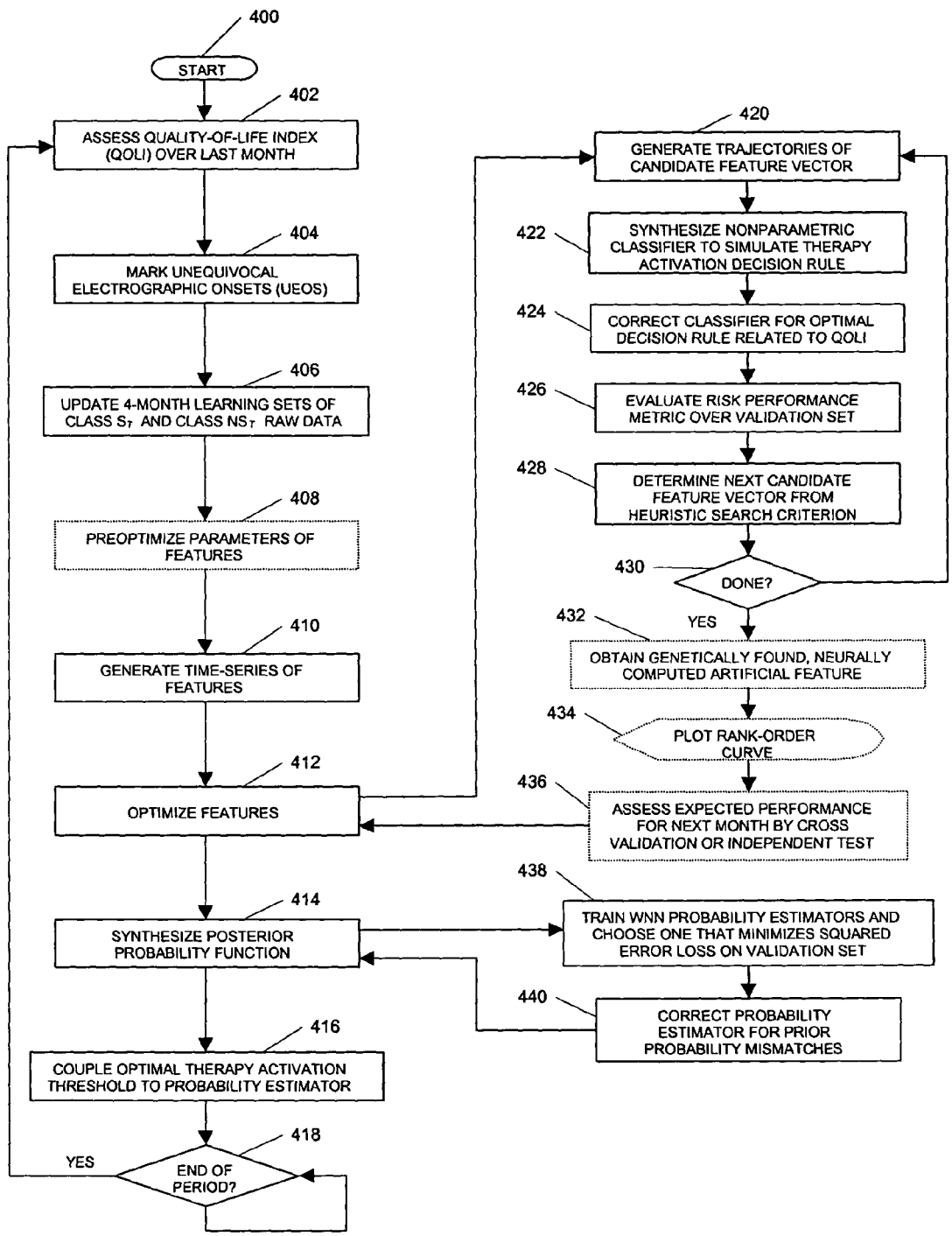
FIG. 4 illustrates a processing logic for the learning algorithm required for the system to improve and maintain performance over time.

Learning in the present inventive system results from a long-term iterative optimization procedure, starting during presurgical evaluation and then periodically thereafter, typically once every month. Patterns of seizure evolution are tracked spanning all treatment periods, including tapered off medication, no treatment, and multitherapy. FIG. 4 illustrates the processing logic of the learning algorithms involved (dotted lines indicate optional steps). The following eight steps and substeps are carried out for each patient and each time scale T except where reference is made to QOLI and unequivocal electrographic onsets (UEOs) (each patient has only one QOLI and one set of UEOs), and to the feature library (there is only one library defined independently of patients and time scales, although it may also be improved from time to time).

Step 1: A quality-of-life index (QOLI) that penalizes the intensity, duration, and frequency of both seizures and treatment interventions (all disturbances to the patient) over time is charted to serve as an overall guide for adjustments and decision making and to document progress (logic block 402).

Step 2: An expert neurologist inspects the IEEG that was digitally archived in the external storage device over the last period, and marks the times of unequivocal electrographic onset (UEO) in all recorded seizures (logic block 404). Optionally, times of asleep-awake states and treatment information are also logged.

Step 3: Based on the UEOs, learning sets of data are created by clipping all the T-minute IEEG epochs immediately preceding seizures and labeling them as "T-minute preseizures" (class $S_T$). Actually, more than exactly T minutes of raw data are clipped, to allow for the initialization period required by historical features. Similarly, randomly chosen, nonoverlapping examples (preferably equal in number to the number of preseizures, or more) of "T-minute nonpreseizures" (class $NS_T$) are clipped and labeled. The latter are preferably chosen to be "baselines" in the sense that they are distanced in both directions of time at least 3T minutes away from the nearest seizure (class S). Note that the above procedure includes examples of "seizure onsets" (class $S_{-1/30}$), defined as the first 2 seconds after UEO, and "nonseizures" (class NS, or more precisely, "nononsets" $NS_{-1/30}$ that qualify as baselines). The class $S_T$ and class $NS_T$ data sets for the last month are joined with the data sets from the three previous months, so that the new month has only an incremental effect on the system. The influence that data will have on learning corresponds to either a 4-month rectangular moving window, or a window that tapers off the last 4 months according to some forgetting schedule (logic block 406).

Step 4: Optionally, parameters associated with the time history of signal features such as observation window length, displacement between window slides (or feature sampling period), and thresholds (on amplitude, duration, density count, etc.) are "preoptimized" using statistical measures of linear separability such as t-scores, Fisher discriminant ratios, K-factors, etc. (logic block 408). A short calibration epoch of class $S_T$ and another of class $NS_T$ are used to generate a time-series of each feature in the feature library under the hypothesized set of parameters for that feature. A parameter set that maximizes separability is chosen by a greedy grid search varying one parameter at a time. Examples can be found in co-pending application Ser. No. (Attorney Docket I080 1020). Direct use of the nonlinear separability measure of Step 6 below is also possible, but research has shown that feature parameters often only marginally affect a classifier's ability to separate the features.

Step 5: Using the feature parameters found in Step 4, or preestablished ones, time-series of all features in the feature library are generated from all the class $S_T$ and class $NS_T$ raw data epochs (logic block 410).

Step 6: An optimal feature vector is searched in the power set of the feature library to minimize the expected overall risk $R_O$ (a classifier-based performance metric that relates to QOLI) or other selected criterion, and real-time computational requirements (logic block 412). For a feature library of size $N_f \leq 30$ and feature dimensions $n \leq 5$, this step can be solved by exhaustive search ($\leq 174{,}436$ evaluations); however, in general, heuristic searches such as add-on-knock-out (an improved version of forward sequential search) are required. Feature optimization involves the steps enumerated herein. Class $S_T$ and class $NS_T$ trajectories of a candidate feature vector are obtained by time-synchronizing the corresponding time-series in Step 5 (logic block 420). Interpolation may be required if the feature sampling periods are different, although they will typically be the same within the same time scale. Nonparametric classifiers that memorize the training data set (randomly chosen vectors typically representing 70% of all the available feature vectors) such as k-nearest neighbors (kNNs), probabilistic neural networks (PNNs,) or hybrids, are synthesized and used to simulate decision rules that are equivalent to each therapy activation unit in FIG. 2 (logic block 422). Their implementation typically does not involve actual probabilities and thresholds, but rather discriminant functions and competitive layers. With the option of tapered-off data influence, the kernel heights of PNN, or the distances in kNN, are weighted with forgetting factors according to the age of each training datum. The classifiers' discriminant functions are corrected to obtain the desired optimal decision rule C*(x) (logic block 424). The overall risk is measured over a validation data set that is not directly used for synthesizing the classifiers (randomly chosen vectors typically representing the remaining 30% of all the available feature vectors), and a score $S = 100 - R_O\%$ is computed for the candidate feature vector/optimal classifier combination (logic block 426). If necessary, the score is penalized to account for computational expense. The next candidate feature vector is determined from the heuristic search criterion (logic block 428), and logic blocks 420-428 are iterated. When finished, the selected feature vector is optionally further processed by a computationally intensive procedure that compresses it into a single genetically-found, neurally computed artificial feature with equal or better discriminatory properties (logic block 432). Optionally, rank-order curves are charted showing score S vs. n for the best n-vectors (logic block 434). Optionally, a measure of expected performance for the next month is obtained by computing an average $R_O$ using v-fold cross-validation over all available data, or over a single independent test set not used in any way during learning (logic block 436). There is a bias-versus-variance tradeoff between these two methods. The expected performance is reported on a point basis (each value of a feature vector counts as one example), consistent with the way in which the real-time system is trained. However, block-basis (a whole epoch counts as one example) tests can also be reported to complement and better comprehend the assessment.

Step 7: Given the optimal feature vector or artificial feature x, the probability function $P(S_T|x)$ is synthesized (logic block 414). Note that there are infinitely many classifiers that can produce the same optimal decision rule in Step 6, but there is only one correct probability function, obtained from $S_T$ and $NS_T$ data independently of the classifiers which define how to act on the probabilities. A wavelet neural network (or other universal approximator suitable for online implementation in a miniaturized device) with a logistic sigmoid output unit is trained to compute $P(S_T|x)$ by presenting $\{0,1\}$ targets and minimizing the expected value of a squared error loss function (logic block 438). This is done using training data while also monitoring error over validation data and choosing the network that minimizes the latter. With the option of tapered-off data influence, training the probability estimator becomes a weighted least squares problem, where the contribution that each squared error makes to the loss function is weighted according to the age of the training datum. The probability estimator's bias term is corrected for prior probability mismatches (logic block 440).

Step 8: The optimal monotherapy activation threshold that corresponds to the same decision rule as the nonparametric classifier of logic block 422 is obtained from a formula and coupled to the probability function $P(S_T|x)$ (logic block 416).

Further details and supporting theory of the above learning algorithm processing logic, required to understand and practice the learning aspects of the invention in its presently preferred and best mode, are now disclosed.

Quality-of-life index. The quality-of-life index (QOLI) is a novel quantitative indicator from 0% to 100% that accounts for not only the intensity, duration, and frequency of seizures over a period of time, but also the severity of treatment and its associated side effects. According to the present invention, QOLI is an exponentially weighted moving average of the daily quality Q, 98% forgotten over a period of a month. The daily quality is the complement of all seizure and treatment disturbances as quantified by their energy buildups over the past day:

$$Q = 100 - \left[ K_S \sum x_{i,j}^2 + K_T \sum u_{i,j}^2 \right],$$

where the first summation is energy of raw EEEG over all channels only during seizures (since the device saves sufficient data around all activations, the neurologist in Step 2 (logic block 404) can determine seizure periods, or it can be automatically determined with a class-S detector); the second summation is energy of the control effort over all channels during all times of activation, both normalized by the worst documented case so that each summation does not normally exceed 100%; and $K_S+K_T=1$ are relative weights for the seizure and treatment terms. Alternatively, the second summation is replaced by a convex sum of the percentages of treatment dosages with respect to their maximum values. Other standardizations from a normative database are also possible. At any given day d, the ongoing QOLI is recursively computed as $$QOLI_d = \lambda Q_d + (1-\lambda) QOLI_{d-1} \text{ with } 0 < \lambda < 1$$

Preferably, prior to prescribing the device, the patient's QOLI is assessed "by hand" to determine if surgery is warranted or as a starting point of reference. $QOLI_0$ is initialized as the weighted average or the mean value of previous Qs, or as 50% if unknown. In expanded form, $QOLI_d$ is a series with a growing number of terms $$QOLI_d = \lambda(1-\lambda)^0 Q_d + \lambda(1-\lambda)^1 Q_{d-1} + \lambda(1-\lambda)^2 Q_{d-2} + \ldots$$

which is a weighted average of present and past Qs with exponentially decaying coefficients that add up to 1 as d goes to infinity. To forget approximately 98% of past data over 30 days, the weights are made to decay like 4 time constants of the natural exponential: $(1-\lambda) = e^{-4/30} = 0.8752$. Therefore, $\lambda = 0.1248$. A QOLI of 0% corresponds to the worst documented case while 100% corresponds to living seizure-free and without any intervention.

The eight-step learning procedure is conceptually an iterative solution to the optimization problem $$\max_{x,\Omega} \int_0^t QOLI(\tau)\mu(\tau)d\tau,$$

where x varies in the space of all possible feature formulas/algorithms, and $\Omega$ varies in the space of all possible mappings from x to multitherapy activation decisions (equivalently, the space of all possible class decision boundaries). That is, the system sets out to find the features and the therapy activation behavior that will maximize the patient's QOLI history weighted by some memory function $\mu(t)$ over time. Obviously, the complexity of the brain alone precludes the possibility of directly solving such problem. In the present invention, the optimization is concretely tackled using lower-level classifier-based performance metrics (described below), obtaining the multitherapy decisions automatically from the monotherapy decisions associated with each time scale. In essence, the optimization problem is converted into multiple simpler problems, one for each time scale:

$$\max_{x,\Omega} E\{S\} \text{ for each } T,$$

where $E\{S\}$ is the expected value for the next month of the score $S=100-R_O\%$ associated with a feature vector/classifier combination. The space of feature vectors x is explored using heuristic search in the power set of a feature library, while the decision boundaries $\Omega$ are implicitly determined from decision rules known to be optimal (described below).

Classifier-based performance metrics. Classifier-based performance metrics are used in the present invention during offline learning to rank the desirability of feature vectors and for researching new features. This is done in terms of classifier outputs as opposed to statistics of the features alone, equivalent to the way in which those features will be transformed online by the multitherapy activation decision logic 60. A note on semantics: detection is a special case of classification where the problem is dichotomous with a "class of interest" (usually with low prior probability) versus a "plain noise" class. In this work, detectors in general are referred to as classifiers, but when referring to seizure detectors, the term is preserved if a distinction from preseizure detection is in order. It is assumed that for every feature vector obtained at the feature-vector sampling rate, the classifier outputs a class decision. Integrating classifier decisions or implementing sequential hypothesis testing before arriving at a declaration (e.g., to eliminate "flickering" of decisions after a detection) can always be reduced to an equivalent "final" classifier by simply using the outputs of the original classifier as input features of the equivalent one. In fact, those are particular examples of historical features. Therefore, there is no loss of generality in the framework presented here. Classifier-based performance metrics have a theoretical definition involving integrals, probability density functions (pdfs), and class decision boundaries, however, their empirical counterparts are presented which are unbiased estimates based on counting. The classifier decisions that are collected from an experiment are tallied and organized into a confusion matrix:

|  | $\hat{S}_T$ | $\hat{NS}_T$ |
|---|---|---|
| $S_T$ | $N_{CP}$ | $N_{FN}$ |
| $NS_T$ | $N_{FP}$ | $N_{CN}$ | where $S_T$ and $NS_T$ are labels for true preseizure and nonpreseizure classes, while $\hat{S}_T$ and $\hat{NS}_T$ indicate the classes declared by the classifier, $N_{CP}$=number of correct positives (preseizure class detections), $N_{CN}$=number of correct negatives, $N_{FP}$=number of false positives (false alarms), and $N_{FN}$=number of false negatives (preseizure class misses). Furthermore, $N_{S_T}=N_{CP}+N_{FN}$=number of preseizure examples; $N_{NS_T}=N_{CN}+N_{FP}$=number of nonpreseizure examples; and $N_{tot}=N_{S_T}+N_{NS_T}=N_{CP}+N_{FN}+N_{CN}+N_{FP}$=total number of examples. The experiment is usually a validation test during training, or an independent test or one of many cross-validation tests during future performance assessment. The examples in an experiment can be defined on a point basis, where a feature vector counts as one example, or a block basis, where a whole signal epoch counts as one example. Results under the two bases are related: point basis and block basis are like high-resolution and low-resolution views, respectively, of the same performance metrics. The block basis is appropriate for reporting because it is easier to comprehend (e.g., "detection delay on a continuous seizure epoch" versus "error risk on random pieces of data"), but not for training the system. What the system is trained to do in real time is give a decision at every feature-vector instant, not wait until the end of a block, using training feature vectors, not time-synchronized training blocks. Also, a block does not allow randomization within the block and severely limits the number of examples available for conducting validation tests. From the confusion matrix, several classifier-based performance metrics can be computed, preferably on a point basis, as shown in Table 1:

TABLE 1

| Quantity | Formula |
|---|---|
| Probability of correct positive = Sensitivity | $P_{CP} = \frac{N_{CP}}{N_{S_T}} = \text{Sens}$ |
| Probability of false negative | $P_{FN} = \frac{N_{FN}}{N_{S_T}} = 1 - P_{CP}$ |
| Probability of correct negative = Specificity | $P_{CN} = \frac{N_{CN}}{N_{NS_T}} = 1 - P_{FP}$ $= \text{Spec}$ |
| Probability of false positive | $P_{FP} = \frac{N_{FP}}{N_{NS_T}}$ |
| Selectivity | $\text{Sel} = \frac{N_{CP}}{N_{CP} + N_{FP}}$ |
| Probability of correct classification | $P_C = \frac{N_{CP} + N_{CN}}{N_{tot}}$ |
| Probability of error | $P_E = \frac{N_{FN} + N_{FP}}{N_{tot}} = 1 - P_C$ |
| Balance | $1 - \frac{2|P_{CN} - P_{CP}|}{|P_{CN} - 0.5| + |P_{CP} - 0.5| + 1}$ |

At any instant in feature time, $P_{FP}$ in the above table is the probability that the next class-$NS_T$ feature vector sample (which for practical purposes is any of approximately all samples) will be a false positive. Under the frequentist view of probability, this is the average number of false positives per feature sampling period. The more widely reported false-positives-per-hour (FPH) can be computed from $P_{FP}$ as the number of point-basis FPs expected in one hour:

$$FPH = \frac{3600 \, P_{FP}}{T_f},$$

where $T_f$ is the feature sampling period in seconds. Again, this relation holds under the assumption that $P(NS_T) \approx 1$. The FPH figure is appropriate for block-basis reports, but can be misleading because of its dependence on $T_f$. For example, a seizure detector with 1 FP per hour is considered acceptable, but it could be a failed system that outputs only 1.1 decisions per hour. The quantity called selectivity in the table is an alternative definition of specificity that indicates how many of all the detected preseizures were specifically preseizures. The quantity called balance is 0 for the worst case when $(P_{CN}, P_{CP}) = (0,1)$ or $(1,0)$, and is 1 in the best case when $P_{CN} = P_{CP}$. Prior probability estimates also follow from the confusion matrix as shown in Table 2:

TABLE 2

| Quantity | Formula |
|---|---|
| Prior probability of preseizure | $P(S_T) = \frac{N_{S_T}}{N_{tot}}$ |
| Prior probability of nonpreseizure | $P(NS_T) = \frac{N_{NS_T}}{N_{tot}}$ $= 1 - P(S_T)$ |

The above performance metrics and estimates are not all independent. At most four equations are required to determine all entries in the confusion matrix, and thus all the listed quantities. Therefore, at most four of the above measures can be independent (e.g., $P_{CP}$, $P_{FP}$, $P_C$, and Sel form one such set). Average detection delay $T_D$ is another classifier-based performance metric that is appropriate for block-basis reports. However, it is not independent of some of the point-basis quantities either. For example, it is not possible for a seizure detector to have long detection delays and at the same time high probability of correct classification (every feature vector during the delay period counts as a point-basis false negative).

From the total probability theorem (or from the counts in the above tables), the probability of error can also be written as $$P_E = P(E|S_T)P(S_T) + P(E|NS_T)P(NS_T)$$
$$= P_{FN}P(S_T) + P_{FP}P(NS_T).$$

Thus, $P_E$ penalizes the two types of detector error (FNs and FPs) with relative weights that are the prior probabilities of the classes. In the context of the present invention, it is usually not enough to penalize false negatives with $P(S_T)$, which is very small for the key time scales in the range of a few hours or less. False negatives, especially for seizure events, are considered intolerable. The error risk metric assigns risk factors $r>0$ to the errors, so that their relative costs can be accounted for:

$$R_E = P_{FN}P(S_T)r_{FN} + P_{FP}P(NS_T)r_{FP},$$

where $r_{FN}$ is a risk factor associated with missing preseizures, and $r_{FP}$ is a risk factor associated with declaring false positives. The relative sizes of these risk factors should be chosen as if assuming that the prior probabilities are equal $P(S_T) = P(NS_T)$. The experienced practitioner can also make a judicious choice of the penalty weights $\pi$ directly in the formula:

$$R_E = P_{FN}\pi_{FN} + P_{FP}\pi_{FP}.$$

Typically, missed seizures are considered so much worse than false alarms that $\pi_{FN} > \pi_{FP}$ (this overrides the effect of low $P(S_T)$, e.g., $\pi_{FN} = 0.75$ and $\pi_{FP} = 0.25$), but exactly how much can be based on the patient's untreated seizure frequency, forms of therapy, or other factors. Ultimately, the choice of risk or penalty factors should lead to long-term QOLI improvement.

When the invention is practiced as a monotherapeutic device using only the seizure detector-controller $g(P_{-1/30}(t), \theta^*_{-1/30})$, the error risk performance metric may be sufficient.

This metric penalizes the allowance of seizures or detection delays (via point-basis FNs) and the unnecessary activations (FPs). However, when one or more predictors-controllers are involved, false positives during online operation become indistinguishable from the successful outcomes of therapy (the correct positives for which seizures were prevented). That is, there will be times when therapy is activated due to predictions and no seizure is recorded, but it is unknown whether a seizure was actually going to occur. This paradoxical condition arises in seizure-preventive systems (it is not an issue in strictly seizure-responsive systems provided that seizure initiation can be unequivocally confirmed) but was never addressed heretofore. According to the present invention, the information on whether online activations were false or true positives is partially available through the higher-level QOLI metric, which penalizes all disturbances to the patient: seizures, and both necessary and unnecessary activations. At times, it may be that a better solution, according to QOLI, is to suppress therapy during those ambivalent times. The only adverse effect of the FP/CP dilemma is that the size of the learning sets will be initially reduced, or the labeling of classes will not be accurate. In the first scheme, all epochs containing ambivalent false/true positives (activations that did not lead to a confirmed seizure), some of which could have served as examples of preseizures and the rest as nonpreseizures, are excluded from the learning sets. The system will still learn to reduce FPs and FNs as usual from epochs before actual recorded seizures and from baselines. During offline learning, the FP/CP ambivalence does not exist because there is no therapy in the software simulations. However, if it is observed that QOLI is worsening, it may be hypothesized that these cases were false positives and can be added as preseizures to the learning sets, until the index improves and stabilizes at a steady state. This may involve some oscillations. For example, if the system is operating in such a way that no actual seizures are recorded by the end of a period, then no new preseizure data will be available for updating the learning sets. This may imply a satisfactory but not necessarily the best achievable QOLI. The system may then start reducing therapy via FP hypotheses, sometimes temporarily worsening QOLI, until an optimum level is achieved at equilibrium. In an alternative scheme, the ambivalent epochs are not excluded, and are randomly assigned $S_T$ and $NS_T$ labels for use with the overall risk performance metric.

The overall risk generalizes the error risk metric to include risk factors for correct classifications too:

$$R_O = P_{FN}P(S_T)r_{FN} + P_{FP}P(NS_T)r_{FP} +$$
$$P_{CN}P(NS_T)r_{CN} + P_{CP}P(S_T)r_{CP},$$

or in terms of penalties, $$R_O = P_{FN}\pi_{FN} + P_{FP}\pi_{FP} + P_{CN}\pi_{CN} + P_{CP}\pi_{CP}.$$

Similar to QOLI, $R_O$ penalizes all therapy activations and is generally the preferred classifier-based performance metric for influencing QOLI. There is no reason to penalize the system for correct negatives, which prolonged would lead to the ideal 100% QOLI, so $\pi_{CN}$ is always zero. Penalties would typically be $\pi_{FP}$='medium', $\pi_{FN}$='very large', $\pi_{CP}$='small', and $\pi_{CN}$=0. After presurgical evaluation, all online FPs and most CPs (the ones that prevent seizures) of a seizure predictor-controller will be ambivalent. As previously explained, these epochs can be initially ignored because it is not known whether to label them as class $S_T$ or $NS_T$ for learning. However, $R_O$ can be measured without difficulty from the remaining epochs. In the alternative scheme, random hypotheses are made regarding the classes of epochs, and penalties are equally assigned to FPs and CPs. Thus, penalties would be $\pi_{FP}$='between small and medium', $\pi_{FN}$='very large', $\pi_{CP}$='between small and medium', and $\pi_{CN}$=0.

Table 3 summarizes the last set of classifier-based performance metrics.

TABLE 3

| Quantity | Formula |
| --- | --- |
| False-positives-per-hour | $FPH = \dfrac{N_{block\,FPs}}{N_{1\text{-hr blocks}}}$ $\approx \dfrac{3600 P_{FP}}{T_f}$ |
| Average detection delay | $T_D = \dfrac{\sum T_{D\,block\,i}}{N_{detection\,blocks}}$ |
| Error risk | $R_E = P_{FN}\pi_{FN} + P_{FP}\pi_{FP}$ |
| Overall risk | $R_O = P_{FN}\pi_{FN}(+P_{CN}\pi_{CN}) + P_{FP}\pi_{FP} + P_{CP}\pi_{CP}$ |

Optimal decision rules. For the same feature vector x, different classifiers can achieve different values of the performance metrics (e.g., probability of false positive). An optimal decision rule singles out the best classifier $C^*(x)$ in the space of decision boundaries $\Omega$, with one or more performance metrics satisfying a desired set of criteria (e.g., minimum probability of false positive subject to a fixed probability of false negative). Actually, infinitely many classifiers can yield the same optimal decision rule as long as they imply the same class decision boundaries, but only some, preferred according to the present invention, are amenable to corrections described hereinafter. Recall from the eight-step procedure of FIG. 4 that classifiers C(x) are used in the present invention during offline learning to facilitate the search for decision rules which are later implemented online by means of probability estimates and thresholds as in FIG. 2.

Six optimality criteria are described below: maximum likelihood, minimum error (maximum a posteriori), Neyman-Pearson criterion, minimum error risk, minimax error risk, and minimum overall risk. The achievement of 100% detection rate with minimal false positives (a Neyman-Pearson type of criterion) is commonly cited in the prior art as the ideal for a seizure detection system. This is an excellent criterion for researching new feature libraries. However, with automatic treatment involved, the ideal must also consider control effort/side effects. In addition, as will be seen later, the 100% CP constraint shifts all the "burden" away from the classifier and places currently unrealistic demands (for prediction) on the features. Although all the presented optimality criteria are available for selection by the authorized caregiver during learning periods, minimum overall risk is currently the preferred compromise for practicing the invention with an existing feature library if one or more seizure predictors-controllers are involved.

Maximum likelihood: The likelihood that a feature vector belongs to class $C_i$ is simply the "height" of the class-conditional probability density function (PDF) $p(x|C_i)$ when evaluated at x.

The maximum-likelihood estimate of the class is $$C(x) = \underset{C_i \in \{S_T, NS_T\}}{\arg\max} \{p(x|S_T), p(x|NS_T)\}.$$

The above equation simply says, "output the argument $C_i$ for which $p(x|C_i)$ is maximum, as $C_i$ takes on values from the set of classes $\{S_T, NS_T\}$." In terms of a threshold on the likelihood ratio, the decision rule declares class $S_T$ if $$\frac{p(x|S_T)}{p(x|NS_T)} > 1.$$

Recall that PDFs are greater than or equal to zero and integrate to 1 in $R^n$, but each PDF can have a different maximum height, and each height can be between zero and infinity. Also note that the likelihood ratio can vary from 0 to $\infty$.

As will become apparent from the following discussion, for a given feature vector x (as a set of feature formulas/algorithms, not numbers), the maximum-likelihood rule solves the problem $$\min_{\Omega}\{P_{FN} + P_{FP}\},$$

giving equal weights to the errors independently of the prior probabilities of the classes. In terms of a threshold on the posterior probability, the decision rule declares class $S_T$ if $$P(S_T|x) > P(S_T).$$

Note that this threshold is very small if $S_T$ is a rare event.

Minimum error (maximum a posterior): For a given feature vector, the problem to solve is $$\min_{\Omega} P_E.$$

With a single binary $\{0,1\}$ classifier output and $\{0,1\}$ target codes for the classes $\{NS_T, S_T\}$, the problems of minimum mean absolute error and minimum mean squared error yield the same result as minimum $P_E$. The minimum-error classifier is the maximum a posteriori estimator of the classes. That is, a classifier makes, on average, the least number of misclassification errors if it always assigns x to the class it most probably belongs to:

$$C(x) = \underset{C_i \in \{S_T, NS_T\}}{\arg\max} \{P(S_T|x), P(NS_T|x)\},$$

where $P(S_T|x)$ is the posterior probability of class $S_T$ given the observation x, and $P(NS_T|x) = 1 - P(S_T|x)$ is its complement. In terms of a threshold on the posterior probability, the decision rule declares class $S_T$ if $$P(S_T|x) > 0.5.$$

Note that the 0.5 threshold does not imply that the classifier can "easily" declare $S_T$ simply because half of the interval [0,1] corresponds to that class. If $P(S_T)$ is very small, it can be extremely difficult to see $P(S_T|x)$ reaching 0.5 (the few times when x becomes imcompatible with the $NS_T$ class). On the other hand, for large T, the prior probability is close to 1, and the probability function will most often exceed 0.5. The prior probability information, which is built into the $P(S_T|x)$ function, is what predisposes the minimum-error classifier to declare "easily" or "hardly."

To obtain the function $P(S_T|x)$ from data by brute force, one would slice the input space into a number of hypercells and count the frequencies of $S_T$ when x was observed in each cell. However, it is more practical to start off from Bayes' theorem:

$$P(S_T|x) = \frac{p(x|S_T)P(S_T)}{p(x)}$$
$$= \frac{p(x|S_T)P(S_T)}{p(x|S_T)P(S_T) + p(x|NS_T)P(NS_T)}.$$

This formula does not in itself ameliorate the well-known "curse of dimensionality," but it leads to a convenient simplification when applied to minimum error classifiers, deals with the more informative class-conditional PDFs, and allows the derivation of corrections for data that do not reflect the true prior probabilities. Applying the formula on the complement class, $P(NS_T|x) = p(x|NS_T)P(NS_T)/p(x)$, note that the denominator is the same, so only the numerator is needed to decide the class:

$$C(x) = \underset{C_i \in \{S_T, NS_T\}}{\arg\max} \{p(x|S_T)P(S_T), p(x|NS_T)P(NS_T)\}.$$

The class-conditional PDFs scaled by their prior probabilities, $p(x|S_T)P(S_T)$ and $p(x|NS_T)P(NS_T)$, will be referred to as "Bayes numerators." Class $S_T$ is declared whenever the Bayes numerator for $S_T$ exceeds that of $NS_T$. In terms of a threshold on the likelihood ratio, $$\frac{p(x|S_T)}{p(x|NS_T)} > \frac{P(NS_T)}{P(S_T)}.$$

Note that the likelihood ratio on the left-hand side can be estimated independently of prior probabilities (each class-conditional PDF comes from data within the $S_T$ or $NS_T$ universes, without any regard to their proportions). The right-hand side is an easily estimated constant threshold that is between 0 and $\infty$. For small $P(S_T)$, the threshold on the likelihood ratio will be relatively large (e.g., 199 for $P(S_T) = 0.005$). This is consistent with that fact that the small prior probability gives small weight to misclassifying $S_T$, making the minimum-error classifier "reluctant" to declare $S_T$. Also note that in the special case of equal prior probabilities for all the classes, the minimum-error and maximum-likelihood rules become equivalent.

Neyman-Pearson criterion: The Neyman-Pearson criterion is a decision rule for detectors that usually refers to choosing a constant false-alarm rate while minimizing the false-negative rate. In the present invention, the optimality criterion of interest is (swapping the classes) minimum probability of false positive subject to the constraint of a fixed probability of false negative. For a given feature vector, the problem to solve is $$\min_{\Omega} \{P_{FP} \mid P_{FN} = K_0\}.$$

It is not possible to give an explicit formula for the decision rule because the decision boundaries vary with the particular pair of class-conditional PDFs, but the answer will still be a threshold on the likelihood ratio (otherwise, the system would give inconsistent rules such as declare $S_T$ if $P(S_T|x)$ >0.8 or <0.3). Geometrically, the fixed FN "area" (really volume in n dimensions) below $p(x|S_T)$, which covers the region $\Omega_{NS_T} \subset R^n$ where x is declared as nonpreseizure, should be distributed (disjointly if necessary) so that the FP area below $p(x|NS_T)$, which covers the "complement" region $\Omega_{S_T}$ where x is declared as preseizure, is as small as possible. This last area is usually in the "tails" of $p(x|NS_T)$. However, in systems such as seizure detectors where the FN area ($P_{FN}$) is forced to be almost zero, $\Omega_{S_T}$ basically covers the whole feature space $R^n$. Therefore, the only sensible way of reducing FPs under the constraint of 0 FNs is to look for different, more separable features. The problem to be solved becomes $$\min_{x,\Omega} \{P_{FP} \mid P_{FN} = K_0\}.$$

With features that do not overlap too much, $\Omega_{S_T}$ can cover just enough space to satisfy the high sensitivity requirement, while at the same time leaving room for $\Omega_{NS_T}$ to produce a reasonable specificity.

Minimum error risk: For a given feature vector, the problem to solve is $$\min_{\Omega} R_E.$$

Compared to the minimum-error rule, the relative weights for the conditional PDFs change from $P(S_T)$ and $P(NS_T)$, to $P(S_T)r_{FN}$ and $P(NS_T)r_{FP}$. The optimal decision rule becomes $$C(x) = \arg\max_{C_i \in \{S_T, NS_T\}} \{p(x|S_T)\pi_{FN}, p(x|NS_T)\pi_{FP}\}.$$

In terms of a threshold on the likelihood ratio, the decision rule declares class $S_T$ if $$\frac{p(x|S_T)}{p(x|NS_T)} > \frac{P(NS_T)r_{FP}}{P(S_T)r_{FN}} = \frac{\pi_{FP}}{\pi_{FN}}.$$

In terms of a threshold on the posterior probability, the decision rule declares class $S_T$ if $$P(S_T|x) > \frac{1}{1 + r_{FN}/r_{FP}}.$$

As in the maximum-likelihood rule, this threshold can be very small if $P(S_T)$ is very small. For example, with $P(S_T)$= 0.005, and even more emphasis on avoiding FNs than maximum likelihood: $\pi_{FN}$=0.75 and $\pi_{FP}$=0.25, the threshold is 0.0017.

Increasing the risk of FPs raises the probability threshold, reducing the system's propensity to declare $S_T$. Similarly, increasing the risk of FNs lowers the threshold, making the system more sensitive. If instead of the above thresholds on the likelihood ratio or the probability, some other constant is used, the classifier's operating point moves along the "receiver operating characteristic" (ROC; $P_{CP}$ vs. $P_{FP}$) curve, trading off the ability to detect preseizures for the ability to detect nonpreseizures (and losing optimality as initially defined by the performance metrics, of course). Changing these simple thresholds on the likelihood ratio or the probability implies that the classifier's complex decision boundaries also change in the n-dimensional space of features. Except for academic special cases, separately thresholding one-dimensional features, as commonly found in prior art systems, creates suboptimal decision rules. For two or more features, the resulting suboptimal decision regions are piecewise rectangular, with boundaries parallel to the feature axes.

As a degenerate special case, a feature vector may have posteriors $P(S_T|x)$ that are always equal to the prior $P(S_T)$. This implies that the feature vector behaves identically under preseizure and nonpreseizure conditions (its class-conditional PDFs are the same $p(x|S_T)=p(x|NS_T)$). The optimal classifier would be the constant-output classifier given by $$C = \arg\max_{C_i \in \{S_T, NS_T\}} \{P(S_T)r_{FN}, P(NS_T)r_{FP}\}.$$

This will be the constant '$NS_T$' for short-term prediction horizons (unless the risk factors offset this), and '$S_T$' for longer T. In terms of the online implementation with probability and threshold as in FIG. 2, the input to the activation decision logic 60 is the constant $P(S_T)$, and so the output will also be a constant: either "intervene forever" or "do not intervene ever." For prediction horizons in the range of greatest interest (from −2 seconds to a few hours), $P(S_T)$ is small, and the decision could be to remain off all the time. For longer horizons T, when the patient's natural interseizure period becomes comparable to T, $P(S_T)$ quickly approaches 100% and the decision will be to intervene in purely open loop, just like traditional medication regimes. According to the present invention, this worst-case scenario can only occur in the rare instance of a patient for whom no feature can be found to separate seizure states. In extensive research, no patient has presented this difficulty to date.

Minimax error risk: For a given feature vector, the problem to solve is $$\min_{\Omega}\left\{\max_{P(S_T)} R_E\right\},$$

considering $P(S_T)$ as an unknown (anywhere between 0 and 1). The error risk metric can also be written as $$R_E = P_{FN} P(S_T) r_{FN} + P_{FP}[1 - P(S_T)] r_{FP}$$
$$= [P_{FN} r_{FN} - P_{FP} r_{FP}] P(S_T) + P_{FP} r_{FP}.$$

For a given set of decision boundaries, this equation has the form of a straight line segment in the variable $P(S_T)$, with starting point at the coordinates $(P(S_T),R_E)=(0,P_{FP}r_{FP})$ and ending point at $(1,P_{FN}r_{FN})$. If decision boundaries are chosen such that $P_{FN}r_{FN}>P_{FP}r_{FP}$, the slope of the line segment is positive and the worst (maximum) $R_E$ occurs at the ending point. If decision boundaries are chosen such that $P_{FN}r_{FN}<P_{FP}r_{FP}$, the slope of the line segment is negative and the worst $R_E$ occurs at the starting point. The more inclined the slope (positive or negative), the worse the maximum $R_E$ becomes. The minimum of this worst-case $R_E$ occurs when decision boundaries are chosen such that $$P_{FN}r_{FN}=P_{FP}r_{FP}.$$

In this case, the slope of the line is zero and $R_E$ becomes independent of $P(S_T)$. Note that without risk factors, this criterion is equivalent to maximizing the balance performance metric. It also minimizes the maximum error rate $P_E$, or equivalently, minimizes the maximum of the two types of detector errors: FNs and FPs.

Minimum overall risk: For a given feature vector, the problem to solve is $$\min_{\Omega} R_O.$$

The optimal decision rule is $$C(x) = \underset{C_i \in \{S_T, NS_T\}}{\arg\max} \{p(x|S_T)[\pi_{FN} - \pi_{CP}], p(x|NS_T)[\pi_{FP} - \pi_{CN}]\}.$$

In terms of a threshold on the likelihood ratio, the decision rule declares class $S_T$ if $$\frac{p(x|S_T)}{p(x|NS_T)} > \frac{P(NS_T)[r_{FP} - r_{CN}]}{P(S_T)[r_{FN} - r_{CP}]} = \frac{[\pi_{FP} - \pi_{CN}]}{[\pi_{FN} - \pi_{CP}]}.$$

In terms of a threshold on the posterior probability, the decision rule declares class $S_T$ if $$P(S_T|x) > \frac{1}{1 + \frac{r_{FN} - r_{CP}}{r_{FP} - r_{CN}}}.$$

Once again, this threshold can be very small if $P(S_T)$ is very small. For example, for $P(S_T)=0.005$, and $\pi_{FP}=0.5$, $\pi_{FN}=0.95$, $\pi_{CP}=0.15$, and $\pi_{CN}=0$, the threshold would be 0.625 on the likelihood ratio or 0.0031 on the posterior probability. For the random hypotheses alternative scheme with $\pi_{FP}=0.25$, $\pi_{FN}=0.95$, $\pi_{CP}=0.25$, and $\pi_{CN}=0$, the threshold would be 0.3571 on the likelihood ratio or 0.0018 on the posterior probability. Recall that these low thresholds do not imply that therapy is "too easily" activated. For these cases of very small $P(S_T)$, the time plot (in the personal computer where the software interface runs) of $P(S_T|x)$ remains close to zero most of the time until abrupt changes occur at times of declaration. For better visualization of small changes close to zero and the transition periods, the logarithm of $P(S_T|x)$ can be plotted instead. When the device itself is built around a small microprocessor (e.g., an 8-bit system), the probability estimators for short T's should directly output Claw or other compounded values, so that the majority of digital codes are assigned to the small (and more frequent) values of $P(S_T|x)$.

Some of the above concepts may seem counterintuitive (e.g., decision rules with low thresholds, or purposeful misclassifications) because everyday experience makes individual probabilistic thinking "linear", i.e., individuals feel comfortable with class $C_i$ given x if they have seen x predict $C_i$ more often than not (maximum a posteriori rule), with a subconscious idea of the classes being essentially equally likely. The following is a simplistic pedagogical aid to understand some of the issues by analogy. Suppose there is a bag full of green balls and a few orange balls. Only one out of every 200 balls is orange. Thus, $P(G)=0.995$ and $P(O)=0.005$. Some balls have a dark spot feature that is highly indicative of "orangeness": when a dark spot is seen, 9 out of 10 times the ball is orange. Thus, $P(O|x=1)=0.9$. Despite this high selectivity, the sensitivity of the "spot test" is lower: only 60% of all orange balls have the dark spot. Thus, $P(x=1|O)=0.6$. Several other probabilities can be derived, for example, the prior probability of a spot $P(x=1)=P(x=1|O)P(O)/P(O|x=1)=0.0033$, the prior of no spot $P(x=0)=1-P(x=1)=0.9967$, a spotless orange ball $P(x=0|O)=1-P(x=1|O)=0.4$, a green ball with a spot $P(x=1|G)=[P(x=1)-P(x=1|O)P(O)]/P(G)=3.35(10)^{-4}$, etc. Suppose a curtain is draped in front of the bag so that balls can be drawn without seeing their color. The minimum-error rule based on a priori knowledge is to always declare G. If however, similar to the prisoner's dilemma, the penalty for missing a green ball is moderate but death for missing an orange ball, then obviously the decision rule changes to always declare O. Now suppose a black-and-white camera and monitor are set up so that the color cannot be seen, but the dark spot on a ball can be seen if it exists. For every spotless ball drawn, compute (or obtain from a look-up table) the probability that it is orange as $P(O|x=0)=P(x=0|O)P(O)/P(x=0)=0.002$. If the dark spot is seen, this changes to $P(O|x=1)=0.9$. Therefore, the time series of $P(O|x)$ has the form $$\{0.002, 0.002, \ldots 0.002, 0.9, 0.002, 0.002, \ldots\}$$

and the minimum-error classifier will only occasionally declare O (whenever it sees the spot). This will be accomplished with an error rate $P_E=P_{FN}P(O)+P_{FP}P(G)=P(x=0|O)P(O)+P(x=1|G)P(G)=0.23\%$. Because the feature x is binary in this example, the minimum-risk decisions are the same as minimum-error unless the threshold on probability is placed below 0.002, which would produce a constant-output O.

This increases sensitivity from 60% to 100%, but the error rate jumps to 0(0.005)+1(0.995)=99.5%. With continuous features, the time series of the probability function is not just two-valued, for example,

{0.0015, 0.0018, ... 0.0017, 0.2, 0.9, 0.0014, ... } so a low threshold that minimizes a risk is not necessarily the extreme risk case/constant-output classifier. Note that an optimal choice of threshold cannot do more than yield the best-achievable performance metric for a given feature vector. If no value of threshold can produce a satisfactory performance then, as previously explained, the burden is on researching for improved features (e.g., perhaps the distribution of dark spots on a ball, dark streaks, etc.).

To complete the analogy with a hypothetical application, consider the green balls as nonpreseizure observation windows (defined by the most recent data point in the window being class $NS_T$), and the orange balls as preseizure observation windows. The dark spot feature is a prodrome 90% of the times seen preceding a seizure. Only 60% of the patient's seizures are stereotyped, so these prodromes are not seen in the remaining 40%. Ten percent of prodromes do occur during nonpreseizure times. The colors, curtain, and black-and-white camera/monitor symbolize the fact that all the underlying phenomena giving rise to seizures in a brain cannot be fully observed, but better results can be achievable than provided by open-loop seizure control by measuring features x from electrophysiological signals or other correlates of seizure, and closing the control loop based on them.

Nonparametric classifiers. Parametric classifiers rely on assumptions regarding feature distributions, from which a few parameters are estimated such as mean vectors and covariance matrices in a Gaussian model. Classifiers based on universal approximators such as neural networks and fuzzy systems have a theoretically infinite set of parameters and learn from examples without relying on assumptions about feature distributions, but typically consume much of the computational resources during training. Nonparametric classifiers have basically no parameters and no learning rules. Training is extremely fast because the entire training data set is simply memorized (stored). The savings on training more than compensate for the CPU time and memory expense incurred during application of nonparametric classifiers, so they are used in the present invention to expedite feature optimization, which may involve hundreds or thousands of tests.

The k-nearest neighbor (kNN) classifier is a nonparametric, nonlinear classifier widely accepted for benchmarking. Given an input pattern vector, the kNN searches for the k most similar (closest in Euclidean distance) vectors in the training database, and declares the corresponding target class by majority vote. A discriminant function score $D_i(x)$ can be derived for each class $C_i$ by counting the "popularity" of each class among the k classes:

$$D_i(x) = \sum_{m=1}^{k} v_{im},$$

where $v_{im}$ is the vote (0 or 1) made for $C_i$ by the $m^{th}$ nearest neighbor. These popularity scores can only range from 0 to k, and their sum must equal k. For example, for k=3 and two classes, $S_T$ may receive 0 votes while $NS_T$ receives 3 votes (or 1 and 2, or 2 and 1, or 3 and 0). The shape of these kNN discriminants directly (though crudely) approximate the shape of posterior probabilities $P(C_i|x)$.

The method of Parzen windows applied to classification, or kernel discriminant analysis, is a classical technique in statistics reinvented as the probabilistic neural network (PNN). With proper corrections, the PNN or its variants can approach optimal decision rules as the number of training observations $N_{obs}$ goes to infinity. Typically, a radially symmetric Gaussian node (Parzen window) is centered at each training input vector pattern $p_j$. The width of all these windows is controlled by a common bandwidth or smoothing parameter. Here, we use an inverse bandwidth parameter $b=(\sigma\sqrt{2})^{-1}$, where $\sigma$ is the standard deviation of the Gaussian kernel. For $N_c$ classes, the output targets $t_j$ are encoded in 1-of-$N_c$ binary vector format $[t_{1j} \, t_{2j} \ldots t_{tN_cj}]$, where only one of these $t_{ij}$'s is equal to 1 at the position i that indicates class $C_i$, and all others are zero. Given an input vector x, the discriminant function for each class $C_i$ is computed as $$D_i(x) = \sum_{j=1}^{N_{obs}} t_{ij} e^{-b\|x-p_j\|^2}.$$

This is the sum of all the Gaussian "bells" that were obtained from class $C_i$, evaluated at x. The shapes of these discriminants are like class-conditional histograms: they approximate the shape of Bayes numerators (class-conditional PDFs scaled by prior probabilities) $p(x|C_i)P(C_i)$.

In an alternative PNN, the discriminant function for each class is $$D_i(x) = \frac{1}{N_i} \sum_{j=1}^{N_{obs}} t_{ij} e^{-b\|x-p_j\|^2},$$

where $N_i$ is the number of training vectors belonging to class $C_i$, that is, $$N_i = \sum_{j=1}^{N_{obs}} t_{ij}.$$

Note that division by $N_i$ produces discriminant function surfaces which are the average of all kernels for each class. These surfaces crudely approximate the shape of class-conditional densities. The maximum value that the estimated curves can attain is 1 (which happens if all examples of a class are identical). When the PDFs have different spreads, the heights will be different. It is seen that the averaging makes this PNN blind to prior probabilities. To illustrate, if there are one million examples of one class and only one example of the other, then dividing by $N_1=10^6$ and $N_2=1$ bounds each estimated curve by a maximum value of 1, irrespective of the constituents' proportions.

As the inverse bandwith parameter b of PNNs becomes large, the Parzen windows become very "thin," so that only the training bell closest to the input vector is significantly activated. The resulting decision rule is therefore identical to the nearest neighbor rule (kNN with k=1). In practice, PNNs should not be used as a kNN, however, because the extremely small values of the Gaussian for far input patterns cause occasional numerical problems such as underflow and division-by-zero.

Before going through a competitive layer (maximum selector) to declare a class, the discriminant functions of these classifiers can be convexly normalized so that their sum across classes equals 1:

$$\overline{D}_i(x) = \frac{D_i(x)}{\sum_{i'=1}^{N_c} D_{i'}(x)} \Rightarrow \sum_{i=1}^{N_c} \overline{D}_i(x) = 1.$$

This convex normalization does not change classifier decisions in any way (the class with maximum $D_i$ will also have maximum $\overline{D}_i$), but at least for the first PNN, the values can serve as estimates of posterior probabilities of the classes: $\overline{D}_i(x) \approx P(C_i|x)$. For all classifiers to which this transformation of nonnegative discriminants is applied, the $\overline{D}_i$ approach either 1 or 0 as $\|x81 \to \infty$, so these normalized discriminants resemble continuous posterior probability functions in the domain extremes, where at least one of the classes can be classified with absolute certainty.

Corrections to classifiers for optimal decision rules. Since seizures are relatively infrequent, preseizure feature vectors will exist with very low a priori probability $P(S_T)$ at the most useful T's. Training and/or testing classifiers/predictors with wrong prior probabilities induces a variety of distortions that, if not corrected, lead to biased assessments of suboptimal systems. For example, a system trained in the laboratory using the distorted prior probabilities implicit in the IEEG archives will not yield the highest achievable accuracy, or may not yield the lowest achievable risk with the fixed weights originally intended, etc. In addition, if the system is tested in the laboratory also with wrong prior probabilities, some of the metrics will look better (or worse) than they will actually be in real life on the patient's device. It is known that correction factors can be applied to the discriminant functions of maximum a posteriori neural classifiers, after training, so that systems will perform as though they were optimized with the true prior probabilities. This correction technique can be extended to other types of decision rules. Corrections can also be derived for thresholds, and can be used to change the optimality definition of a given classifier. In addition, corrections can be derived for the posterior probabilities as explained in a subsequent section. The consequences of ignoring these corrections and much of the following methods are not well known judging by the pattern recognition literature, where in fact, the mistake is routinely found.

The a priori probability of preseizure vectors estimated from the proportion of preseizure vector examples in the training data set, $$P^{TRN}(S_T) = \frac{N_S^{TRN}}{N_{tot}^{TRN}},$$

will typically not reflect the true frequency of occurence $P^{true}(S_T)$ in the continuous time line (seizures are accelerated during hospitalization, there are time gaps in the recordings, etc.). The true prior probability is estimated over patient monitoring periods longer than the hospitalization and under steady-state drug, hydration, sleep, and other conditions (though not longer than about a month, when long-term behavior can be considered non-stationary). From Bayes' numerators in the error and risk decision rules, it can be seen that this will cause a mismatch between an optimal classifier learned under the apparent proportions, and what the optimal classifier would have been for the true environment (the correct ROC operating points will be different). This issue must be carefully addressed, particularly when the prior probability for one class is much smaller than for the others. In an attempt to incorporate the true proportions, it is impractical and counterproductive to train a classifier with millions of $NS_T$ vectors and only a few $S_T$ ones. Training a classifier with such an unbalanced proportion of examples would obscure the very patterns it must pay attention to. The correction methods presented here simultaneously account for the prior probability mismatch after training has taken place, and allow the practitioner to use any convenient proportion of examples for training classifiers or probability estimators.

Three types of classifiers are defined based on the type of discriminant functions $D_i(x)$ they construct. Type-B classifiers have an internal representation of the shape of the Bayes numerator for each class, that is, the $D_i(x)$ equal $p(x|C_i)P(C_i)$ or are proportional to them by a common factor across classes. Equivalent classifiers that monotonically transform the Bayes numerator score such as with the negative or the logarithm, from which the score can be recovered, would still qualify as type-B. Bayes quadratic classifiers for jointly Gaussian features and PNNs in the limit $N_{obs} \to \infty$ are examples of type-B classifiers. Type-L classifiers have an internal representation of the shape of the likelihood score for each class, that is, the $D_i(x)$ equal the PDFs $p(x|C_i)$ or are proportional to them by a common factor across classes. A maximum selector of area-normalized histograms and the alternative PNN in the limit $N_{obs} \to \infty$ are examples of Type-L classifiers. Type O are all other classifiers which can yield optimal decision rules but do not attempt to approximate discriminant functions related to $p(x|C_i)$ or $p(x|C_i)P(C_i)$. Fuzzy classifiers and kNNs are examples of type-O classifiers.

A type-B classifier that was optimized using wrong training prior probabilities learns the equivalent of the discriminants $D_i^{TRN}(x)=p(x|C_i)P^{TRN}(C_i)$. The decision rules affected (when implemented as $\text{argmax}\{\cdot\}$) are min $P_E$, and min $R_E$ and min $R_O$ with risks originally fixed through risk factors r. Each discriminant can be corrected by rescaling with correction factors $$c_i = \frac{P^{true}(C_i)}{P^{TRN}(C_i)},$$

so that applying these numbers to the discriminants $$D_i^{true}(x) = D_i^{TRN}(x) c_i,$$

corresponds, within a factor, to canceling the wrong prior probabilities and replacing them with the true ones:

$$p(x \mid C_i) P^{TRN}(C_i) \frac{P^{true}(C_i)}{P^{TRN}(C_i)}.$$

Since PDFs are independent of prior probabilities, type-L classifiers are not inherently affected by prior probability mismatches. They are ideally suited (when implemented as argmax{·}) for the maximum-likelihood decision rule, Neyman-Pearson, minimax $R_E$, and for min $R_E$ and min $R_O$ with risks originally fixed through penalty factors a. The same multiplicative correction technique can be used for changing the optimality definition of a given classifier. For example, if we are given a maximum-likelihood type-L classifier, which minimizes $0.5P_{FN}+0.5P_{FP}$, and later decide it should have been $R_E=0.75P_{FN}+0.25P_{FP}$, then we only need to reemphasize the discriminant function for class $S_T$ with $$D_{S_T}^{new}(x) = D_{S_T}^{TRN}(x)\frac{0.75}{0.5},$$

while similarly deemphasizing the complement class $$D_{NS_T}^{new}(x) = D_{NS_T}^{TRN}(x)\frac{0.25}{0.5}.$$

Of course, type-L classifiers would be affected by prior probability mismatches if they are used to implement the decision rules mentioned above for type-B classifiers by substitution into the formula $D_i^{TRN}(x)=p(x|C_i)P^{TRN}(C_i)$. It should be noted that all classifiers/decision rules are affected by prior probability mismatches when they are implemented as a threshold on the posterior probability $P(C_i|x)$ as in the presently preferred online implementation. The online implementation of direct estimates of PDFs by type-L classifiers is considered infeasible beyond about five feature dimensions.

Type-O discriminant functions can have arbitrary shapes and give optimal classifiers tuned for the apparent prior probabilities $P^{TRN}(C_i)$, as long as their intersections produce the same decision boundaries or thresholds as those produced by $p(x|C_i)$ or $p(x|C_i)P^{TRN}(C_i)$. However, because they are not required to approximate the shape of these likelihood scores or Bayes numerators, there is no guarantee that the above correction techniques will result in type-O classifiers that behave optimally under real-life conditions.

In the kNN, even though its "popularity" score discriminants do not have the shape of $p(x|C_i)P^{TRN}(C_i)$, the correction factors are directly multiplied to those scores prior to entering a competitive layer. In the PNNs, the correction factors are multiplied to the discriminant scores for each class prior to convex normalization and processing by a competitive layer. In our research, kNNs have demonstrated the property that they can be very robustly corrected for prior probability mismatches, though only partially, using the methods outlined here. This may be related to the fact that if a class is rare, then it is inherently less likely to be represented in a nearest neighbor. As types B and L, PNNs can be fully corrected for prior probabilities or new optimality, though the practitioner is warned that the sensitivity on the b parameter can make this difficult. The effect of an inadequate b can outweigh the classifier's rectifiability to the point that no correction is achieved.

Feature subset selection. In building a rich feature library based on a combination of intuition, brainstorming, knowledge of the field, and trial-and-error, no effort is (or should be) made to ensure that the $N_f$ features are uncorrelated. Some of the features may even turn out to be completely irrelevant for the particular prediction task. Furthermore, the use of all features in this library is associated with a large computational burden on the learning and execution process.

Therefore, the smallest feature subset (n-vector) that meets a performance objective must be found. Cover has constructed an example with binary features where the best feature subset was actually the "worst-looking" according to any greedy techniques because independent observations (e.g., through time) of a "bad" feature can yield better accuracy than independent observations of a "good" one. For a feature library of size $N_f \leq 30$ and feature dimensions $n \leq 5$, this selection problem can be solved by exhaustive search ($\leq 174,436$ evaluations), however, in general, heuristic searches are required despite Cover's paradox. For a fixed n, there are $$\binom{N_f}{n} = \frac{N_f!}{n!(N_f-n)!}$$

possible ways of choosing n-dimensional feature vectors out of the $N_f$ features, $n \leq N_f$, which adds up to $2^{N_f}-1$ feature vectors of all possible sizes in the power set of the feature library. These numbers can grow so large as to preclude the possibility of exhaustive search. For example, $$\binom{30}{10}, \binom{100}{5}, \text{ and } \binom{100}{10}$$

are on the order of $30(10)^6$, $75(10)^6$, and $1.7(10)^{13}$, respectively.

One of the simplest strategies to deal with this exponential explosion is the forward sequential search. Each of the $N_f$ features are first individually scored. The best one is picked and made a permanent part of what will become a "growing" feature vector. Among the still unused $N_f-1$ features, the feature that works best in conjunction with the first one is found and added to the feature vector. Then among the still unused $N_f-2$ features, the feature that works best in conjunction with the previous pair is found and added to the feature vector. The process is iterated until n features have been chosen (prefixed or until scores reach a desired level). This technique is a greedy algorithm (the best 1-vector plus another may not be the globally best 2-vector, and so on), but requires only $nN_f-n(n-1)/2$ score evaluations. The numbers in the previous example dramatically drop to 255, 490, and 955, respectively. It has been empirically found in the prior art that the difference in classification performance between forward selection and dynamic programming (a much more exhaustive method) is typically 4% or less. However, because the candidate feature vectors generated by this method are nested sets.

However, to reduce the probability that randomly chosen PDFs can defeat forward (or backward) selection, Stearns' $(N_{add}, N_{ko})$ add-on-knock-out algorithm (originally called "plus m, take away n") is the preferred computationally tractable, heuristic search method for feature selection. The best $N_{add}$ (e.g., 2) features are first added one-by-one as in forward selection, but on the next round, the worst $N_{ko}$ (e.g., 1) are eliminated as in backward selection. This alternating process is iterated until n features are obtained. The method produces a sequence of candidate feature vectors that are not necessarily nested, and typically involves about five times the computational effort of forward sequential search. This is still well below the typical increase required by dynamic programming.

Artificial features. The specification of distinguishable features is the most important key to intelligent sensing. Given a set of features, it is known how to create optimal classifiers. The reverse problem, specifying a set of features given the classifier, has been limited in the art to feature subset selection as described in the previous section. The present invention optionally further optimizes the selected feature vector using a computationally intensive procedure to create a genetically found, neurally computed (GFNC) artificial feature which, by definition, matches or exceeds the performance of the original feature vector. For fixed classifier computational resources, the discrimination task is greatly facilitated with a single GFNC input feature compared to multidimensional inputs carrying the same, but more "hidden" information.

In this framework, features are represented and computed by networks. Since a feature, as defined in the present invention, is obtained from a formula or algorithm that maps a raw input set into a scalar, then a suitable neural network is capable of learning and implementing the mapping. Therefore, GFNC features are obtained from the outputs of feedforward networks, or the stable equilibria of recurrent networks, and can mimic conventional features or be completely novel artificial features. It is envisioned that with future increases in computational capabilities, artificial features will be abstracted directly from raw data, which are thus not limited to information generated from a finite list of features. The networks are represented genotypically as binary strings (chromosomes) and are considered as individuals in a genetic algorithm (GA) or other evolutionary algorithm. Table 4 highlights the contrasting characteristics between conventional and artificial features.

TABLE 4

| Conventional Features | Artificial Features |
|---|---|
| sequential | parallel |
| Von Neumann computer | neural computer |
| programmed | learned |
| combinatorial | inductive |
| ad-hoc | optimized |
| based on intuition | based on data |

As an example of how a GFNC feature can be created, consider the problem of deciding whether two random vectors are parallel in the plane. Given the starting points and increments of the two vectors, $(x_1, y_1, \Delta x_1, \Delta y_1)$ and $(x_2, y_2, \Delta x_2, \Delta y_2)$, it is desired that a decision structure output 1 for parallel, and 0 for non-parallel. It will be instructive to note that the starting points and the relative size of the increments are irrelevant, and from knowledge of analytic geometry, that the absolute value of the cosine between the vectors:

$$|\cos\theta| = \frac{|\Delta x_1 \Delta x_2 + \Delta y_1 \Delta y_2|}{\sqrt{(\Delta x_1^2 + \Delta y_1^2)(\Delta x_2^2 + \Delta y_2^2)}},$$

is an optimal feature for this task, with 0 meaning orthogonal, and 1 meaning completely parallel. Sets of random training and testing input vectors $[x_1, y_1, \Delta y_1, \Delta y_1, x_2, y_2, \Delta x_2, \Delta y_2]$ containing parallel and non-parallel classes are generated. An artificial feature is implemented by an algebraic network, with topological connection symmetries, with single-input nodes that represent one of the unary mathematical operators $\{I(\bullet), (\bullet)^2, \sqrt{|\bullet|}, |\bullet|\}$ where $I(\bullet)$ is the identity operator, and with two-input nodes that represent binary operators $\{+, -, *, /\}$. The latter type of nodes can be easily generalized to n-ary operators. Conventional neural networks can also be employed but would be much larger. The output of the network is a rather general nonlinear feature of the original inputs. Raw training and testing patterns go through the network in order to create a single-input kNN classifier that is trained on the artificial feature, and to compute the $P_C$ accuracy metric on the test set.

The genetic algorithm (GA) uses the $P_C$ metric as a fitness function. Each candidate solution is an artificial feature/formula. In the GA's chromosome for each individual, the node operations can be represented using two binary genes (because there are $2^2$ possible operators per node), for a total of 44 genes per individual. This chromosome is decoded into the network that represents an artificial feature. The evolution of artificial features in the population progresses by genetic crossover and mutation. For a network with 30 nodes, with four possible operators per node, and allowing the topological connections of all inputs to vary as $\{0,0\}$ (no connection), $\{0,1\}$, $\{1,0\}$, and $\{1,1\}$ (two connections), the problem is a combinatorial search in a 38-dimensional space containing $4^{38} \approx 7.6(10)^{22}$ candidate solutions. The age of planet Earth is estimated at $3.5(10)^9$ years. Therefore, if it took only one second to carry out each fitness function evaluation, it would take on the order of 700,000 lives of the Earth to fully enumerate the solution space and guarantee optimality.

In experiments with the above problem, using relevant inputs, a feature never thought of by a domain expert was quickly found to achieve the same zero-error performance as the common-sense analytic feature. When mixing relevant and irrelevant inputs, a significant increase in accuracy (from 55% to 84.2%) was possible by evolving the artificial feature from the raw set of eight inputs within computational resource and time constraints (a few hours in a personal computer). Three of the four delta features ($\Delta x_1$, $\Delta x_2$, and $\Delta y_2$) remained connected, while three of the four starting-point features ($x_1$, $x_2$, and $y_1$) were disconnected. This suggests that the GFNC procedure was attempting to create features that pay more attention to the relevant features than to the irrelevant ones. After pruning disconnected nodes, the analytic form of the resulting artificial feature is $$(\Delta x_1^2 - \Delta x_2^2)\Delta y_2^4 y_2^2.$$

This example illustrates how GFNC artificial features can provide viable solutions in a prohibitively large space, in fact, much larger than the power set of features presented by the original feature library (255 feature subsets in this example).

Probability estimation. The synthesis of realistic posterior probability functions $P(S_T|x)$ is among the key elements of the present invention. In addition to class discrimination, the internal discriminant functions of nonparametric classifiers can also be used for estimation of posterior probabilities. But because these classifiers store all training data to directly estimate class-conditional PDFs, they suffer badly from the "curse of dimensionality" and do not offer much over multidimensional histograms in this respect. Their use (especially online) for feature vectors with more than about five dimensions becomes increasingly more questionable, when good PDF estimation requires on the order of $100^5 = 10,000,000,000$ training tokens. According to the present invention, the function $P(S_T|x)$ is neurally learned from data even though the desired target probabilities are unknown following the method of training a generalizing neural network with a logistic sigmoid output node (to facilitate learning of the [0,1] range), binary {0,1} target outputs y to indicate 'NS$_T$' and 'S$_T$' classes respectively (instead of the actual probabilities), and a squared error loss function such as those based on the mean squared error:

$$MSE = E\{(y - \hat{y})^2\},$$

where y is a desired target (either 0 or 1) and $\hat{y}$ is the output of the network (continuous between 0 and 1) for input x. The binary-target and squared-error conditions cause a correctly trained network to output the mathematical expectation of the {0,1} target output values, given x. That is, the output of the network is, ideally, the expected value of the binary random variable y|x, $$\hat{y} = E\{y|x\} = 0 \cdot P(y=0|x) + 1 \cdot P(y=1|x),$$

which precisely coincides with the desired quantity $P(S_T|x)$. This happens because the minimizer of a squared error loss function is the conditional mean function (here $E\{y|x\}$). Simply put, in the "battle" between contradictory 0 and 1 examples that are presented to the network for a given x, the network settles at the average value because that is what minimizes the squared error at x. This average includes the prior probability information based on the relative proportions of the 0s and 1s. In practice, there may be just one input-output example ($p_j$, $y_j$), not multiple examples, for a given x. This is where the generalizing ability of a neural network comes crucially into play. Although the effects of model approximation and estimation errors in this setting are not well understood, this approach has been immensely successful in practice.

Wavelet Neural Networks. Wavelet neural networks (WNNs) are used in the present invention to learn the probability function $P(S_T|x)$ in up to about 10 dimensions with moderate amounts of training samples. By having wavelet nodes act like "templates" that match the structure of many functions of practical interest, WNNs offer efficient solutions to regression and concept learning problems in general. WNNs can optimally encode information about one-dimensional functions. Multidimensional affine and radial wavelet networks are dense in large spaces, can attain a sup-norm approximation rate that is independent of input dimension, and their number of parameters grows linearly with both dimension and number of nodes, in contrast to the exponential number needed in traditional polynomial, spline, and trigonometric expansions. In addition, WNNs can be initialized in ways that significantly speed up training. In real-world applications ranging from EEG analysis to financial engineering, WNNs have shown a tendency to yield efficient solutions with fewer parameters than alternative network architectures for a given level of accuracy.

The basic implementation of a T-minute WNN probability model is a multiple-input, single-output transformation:

$$P(S_T | x) \approx \hat{y} = \frac{1}{1 + e^{-u}},$$

$$u = \sum_{m=1}^{M} c_m \psi_{A_m, b_m}(x) + c_1^{\text{lin}} x_1 + \ldots + c_n^{\text{lin}} x_n + c_0^{\text{lin}},$$

$$\psi_{A_m, b_m}(x) = \psi\left(\sqrt{(x - b_m) A_m (x - b_m)^T}\right),$$

-continued $$\psi(x) = \min\left\{\max\left\{\frac{3}{2}(1 - |x|), 0\right\}, 1\right\} \cos\left(\frac{3}{2} \pi x\right),$$

where x is presented as a row vector of input features [$x_1 \ldots x_n$], $b_m$ is a translation vector associated with the $m^{th}$ wavelet node, $A_m$ is a symmetric positive semi-definite "squashing" matrix, M is the number of wavelet nodes, c are linear output coefficients associated with a nonlinear portion of the model, and $c^{lin}$ are linear output coefficients associated with a linear portion of the model. The dependence of this WNN on T is implicit by way of the training data set that is used to tune the network parameters $A_m$, $b_m$, c, and $c^{lin}$.

The number of wavelet nodes M can be initialized based on K-means clusterings of the training data in the input-output space for a successively larger number of clusters. Each clustering is assigned a measure of within-to-between-variance of the clusters. The measure is the inverse of a multidimensional F-ratio, $$\frac{\sum_{i=1}^{K} \sum_{j=1}^{N_i} \left\| w_j^i - \overline{w}_i \right\|^2 / (N_{obs} - K)}{\sum_{i=1}^{K} N_i \left\| \overline{w}_i - \overline{w} \right\|^2 / (K - 1)},$$

where $N_{obs}$ is the number of observations, K is the number of clusters, $w_j^i$ is an input-output data point [p y] that belongs to the $i^{th}$ cluster, $N_i$ is the number of such points in the $i^{th}$ cluster, $\overline{w}_i$ is the center of the $i^{th}$ cluster, and $\overline{w}$ is the grand mean. The number of wavelet nodes is taken to be the minimizer of this measure. As a by-product, initial network parameters are obtained from first and second order statistics of the clusters. Alternatively, if computational resources allow it, the WNN can be "grown" from its smallest size to sufficiency based on systematic search and overall performance metrics.

For every hypothesized WNN probability model structure, training of the network parameters $A_m$, $b_m$, c, and $c^{lin}$ is cast as a minimization problem with respect to the empirical average squared error function $$ASE = \frac{1}{N_{obs}} \sum_{j=1}^{N_{obs}} (y_j - \hat{y}_j)^2.$$

With the option of tapered-off data influence, training the probability estimator becomes a weighted least squares problem, where the contribution that each squared error makes to the loss function is weighted by $w_j$ according to the age of the training datum and some forgetting schedule:

$$WASE = \frac{1}{N_{obs}} \sum_{j=1}^{N_{obs}} w_j (y_j - \hat{y}_j)^2.$$

In this case, the most recent of the last four months has only an incremental effect on the system, but typically in such a way that it has more influence than the previous months on the learned probability function.

These error criteria are used as a guide during minimization using the training set, however, care is taken to select a model that attempts to minimize the expected value of this measure over a validation set representative of future data (not over the particular training set). Estimates of E{ASE} can be obtained in principle from regularization techniques, or resampling techniques such as leave-one-out cross-validation and bootstrap statistics. However, split-sample validation is by far the simplest, yet an effective practical technique for discouraging overtraining of the network and thus for attempting to preserve generalization. The data set is randomly split into a training set TRN (e.g., 70% of all ($p_j$, $y_j$) examples) and a validation set VAL (e.g., the remaining 30%). If enough examples are available, a completely independent test set TST can also be reserved for final assessment of generalization error (future performance). Training proceeds by minimization of error over TRN while monitoring the error on VAL. The best WNN on VAL is recorded at every iteration. Typically, the error over TRN drops to arbitrarily small values (provided a complex enough WNN), while the error over VAL first decreases and then increases steadily. The final network chosen is the one that minimizes the error over VAL. Note that minimizing VAL error in this fashion does not imply memorizing VAL (whose associated error can always be driven to zero). VAL is ideally a representative sample of the universe of all future examples. There is a bias introduced by this scheme to the extent that VAL deviates from this ideal. The preferred minimization algorithms for training the WNN are based on a multi-start Levenberg-Marquardt optimization, a genetic algorithm of ranking type, or a combined genetic algorithm global search followed by Levenberg-Marquardt fine tuning. These optimization algorithms and combination schemes are well known in the art.

Coding the continuous function $P(S_T|x)$ as a WNN satisfies low memory and fast throughput requirements for real-time, online operation at the expense of relatively difficult offline training. For low feature dimensionality ($\leq 5$), the function can also be approximated by kNNs or PNNs for fast offline training at the expense of large online memory and slow throughput. Hybrid architectures such as PNN truncated by nearest neighbors, or vector-quantized PNNs are also possible (although the latter is the same as an initialized, untrained radial basis function neural network). With minimal resources, the continuous function can ultimately be discretized and implemented in a binary decision tree (a look-up table with quantized inputs).

Corrections to probability estimators for prior probability mismatches. The posterior probability estimates learned from data sets that do not reflect the true prior probability of the classes (e.g., from EEEG archives or clinical trials) will be distorted. Correcting posterior probability estimates obtained from type-L discriminant functions involves simply plugging the PDFs into Bayes formula with the correct prior probabilities. Correcting estimates obtained from type-B discriminants can be accomplished with correction factors prior to convex normalization:

$$\overline{D}_i^{true}(x) = \frac{D_i^{TRN}(x)c_i}{\sum_{i'=1}^{N_c} D_{i'}^{TRN}(x)c_{i'}}.$$

This corresponds, within a factor, to $$P^{true}(C_i|x) = \frac{p(x|C_i)P^{ijk\aleph}(C_i^{\cdot})\frac{P^{true}(C_i)}{P^{ijk\aleph}(C_i^{\cdot})}}{\sum_{i'=1}^{N_c} p(x|C_{i'})P^{ijk\aleph}(C_{i'}^{\cdot})\frac{P^{true}(C_{i'})}{P^{ijk\aleph}(C_{i'}^{\cdot})}}.$$

The order of correction and convex normalization operations can be switched, but then a second and final convex normalization is required to yield the above result. As previously explained, computational requirements in high dimensions cast serious doubts on the results obtained from the above type-L and B discriminants for probability estimation.

Corrections for online probability estimators are now derived. Bayes' theorem can be written in a form that is compatible with a logistic sigmoid unit $$\frac{1}{1+e^{-u}}$$

at the output of a neural network. The function that the network must indirectly learn from a training data set is $$P^{TRN}(S_T|x) = \frac{p(x|S_T)P^{TRN}(S_T)}{p(x|S_T)P^{TRN}(S_T) + p(x|NS_T)P^{TRN}(NS_T)}.$$

Dividing the Bayes numerator and denominator by the numerator, and using the laws of logarithms, we obtain $$P^{TRN}(S_T|x) = \frac{1}{1 + \frac{p(x|NS_T)P^{TRN}(NS_T)}{p(x|S_T)P^{TRN}(S_T)}}$$

$$= \frac{1}{1 + \exp\left\{\ln\frac{p(x|NS_T)P^{TRN}(NS_T)}{p(x|S_T)P^{TRN}(S_T)}\right\}}$$

$$= \frac{1}{1 + \exp\left\{-\left[\ln\frac{p(x|S_T)}{p(x|NS_T)} + \ln\frac{P^{TRN}(S_T)}{P^{TRN}(NS_T)}\right]\right\}}.$$

It can be seen that the neural network's job prior to the logistic sigmoid output unit is to approximate the term between square brackets: the log-likelihood ratio function (independent of prior probabilities) plus a bias term (dependent on prior probabilities). Therefore to correct $P^{TRN}(S_T|x)$ after having already trained the neural network, all that is necessary is to go inside the network and replace the constant bias term with the correct one. For the WNN, this is $$c_0^{lin} = \ln \frac{P^{true}(S_T)}{P^{true}(NS_T)}.$$

Even if the neural network is given as a black box, if $P^{TRN}(S_T)$ is known, then the ratio of posterior probabilities of the two classes can be used to recover the likelihood ratio:

$$\frac{p(x|S_T)}{p(x|NS_T)} = \frac{P^{TRN}(S_T|x)P^{TRN}(NS_T)}{P^{TRN}(NS_T|x)P^{TRN}(S_T)},$$

which can then be plugged into Bayes formula to compute the corrected probability as $$P^{true}(S_T|x) = \frac{1}{1 + \frac{p(x|NS_T)P^{true}(NS_T)}{p(x|S_T)P^{true}(S_T)}}.$$

An important additional advantage of these correction methods is that training can be done purposely under a balanced (50%-50%) or any other convenient proportion (as they come from the clippings of the IEEG archives), and still obtain the probability estimates for the unbalanced, real-life condition. An increased variance in the unbiased estimate can be expected, of course, just like in any other estimation problem with a reduced sample size.

The present invention is realized in a combination of hardware and software. Any kind of computer system or other apparatus adapted for carrying out the methods described herein is suited. A typical combination of hardware and software could be a general purpose computer system with a computer program that, when loaded and executed, controls the computer system such that it carries out the methods described herein. The present invention can also be embedded in a computer program product which includes all the features enabling the implementation of the methods described herein, and which, when loaded in a computer system is able to carry out these methods.

Computer program instructions or computer program in the present context means any expression in any language, code, or notation or a set of instructions intended to cause a system having an information processing capability to perform a particular function, either directly or when either or both of the following occur: (a) conversion to another language, code or notation; (b) reproduction in a different material form.

In light of the above teachings, those skilled in the art will recognize that the disclosed methods, formulas, algorithms, and embodiments may be replaced, modified, or adapted without departing from the spirit or essential attributes of the invention. Therefore, it should be understood that within the scope of the appended claims, this invention may be practiced otherwise than as exemplified herein.

What is claimed is:

1. A system for automatically predicting and preventing the electrographic onset of a seizure in an individual, comprising:
  a signal acquisition component to condition and digitize a plurality of raw signals received from a transducer implanted in the individual;
  a preprocessor to attenuate any artifacts in the plurality of digitized signals;
  a feature extraction component containing processing logic to select patient-specific seizure-predictive and seizure-indicative attributes from the preprocessed signals to form an optimal feature vector;
  a probability estimator component that synthesizes a probability vector as an estimator of the likelihood of seizure for a plurality of prediction times;
  a multitherapy activation component containing processing logic to determine the therapy modalities that are to be activated or deactivated at any time; and
  an implanted device including a plurality of therapy actuators to automatically activate at least one associated therapy in response to an output signal from the multitherapy activation component.

2. The system for automatically predicting and preventing the electrographic onset of a seizure of claim 1 wherein the therapies associated with the plurality of therapy actuators include one or more of cognitive stimulation, sensory stimulation, biofeedback, electrical stimulation and pharmacological infusion.

3. The system for automatically predicting and controlling the electrographic onset of a seizure of claim 1 wherein the preprocessor is implemented in any one or more of a microprocessor, a digital signal processor, a field programmable gate array, an application specific integrated circuit, and a hybrid analog/digital circuit.

4. The system for automatically predicting and controlling the electrographic onset of a seizure of claim 1 wherein the feature extraction component is implemented in any one or more of a microprocessor, a digital signal processor, a field programmable gate array, an application specific integrated circuit, and a hybrid analog/digital circuit.

5. The system for automatically predicting and controlling the electrographic onset of a seizure of claim 1 wherein the probability estimator component is implemented in any one or more of a microprocessor, a digital signal processor, a field programmable gate array, an application specific integrated circuit, and a hybrid analog/digital circuit.

6. The system for automatically predicting and controlling the electrographic onset of a seizure of claim 1 wherein the multitherapy activation component is implemented in any one or more of a microprocessor, a digital signal processor, a field programmable gate array, an application specific integrated circuit, and a hybrid analog/digital circuit.

7. The system for automatically predicting and controlling the electrographic onset of a seizure of claim 1 wherein the plurality of therapy actuators are programmed to operate in an open loop mode, delivering prophylactic treatment by any one of a button, a magnet, and a vibration transducer.

8. The system for automatically predicting and controlling the electrographic onset of a seizure of claim 1 wherein the plurality of therapy actuators are programmed to operate in a closed loop mode, using any one of a proportional, a proportional-integral-derivative, an optimal continuous, a gain-scheduled, a multilevel, and a bang-bang feedback control strategy.

9. The system for automatically predicting and controlling the electrographic onset of a seizure of claim 1 further comprising an external storage for storing the digitized signals processed by the signal acquisition component.

10. The system for automatically predicting and controlling the electrographic onset of a seizure of claim 1 further comprising a wearable access device to display the probability vector of oncoming seizures and the multitherapy activation status to the individual.

11. The system for automatically predicting and controlling the electrographic onset of a seizure of claim 1 wherein the implanted device further includes an electronically erasable programmable read-only memory for downloading a plurality of learned algorithms and parameters received via transceivers.

12. The system for automatically predicting and controlling the electrographic onset of a seizure of claim 1, further comprising a processor including a centralized learning and programming interface logic for simulating the actions of the feature extraction component, probability estimator component, and multitherapy activation component in order to improve the performance of each component.

13. The system for automatically predicting and controlling the electrographic onset of a seizure of claim 12 wherein the processor is a laptop or workstation computer.

14. The system for automatically predicting and controlling the electrographic onset of a seizure of claim 13 wherein the laptop or workstation computer is at a location different from that of the individual.

15. The system for automatically predicting and controlling the electrographic onset of a seizure of claim 12 wherein the processor is located at a remote facility that is accessible over the Internet via a T1 line or other high speed digital link.

16. The system for automatically predicting and controlling the electrographic onset of a seizure of claim 1 wherein the plurality of therapy actuators automatically apply the minimally required intervention measure, thereby minimizing associated side effects.

17. The system for automatically predicting and controlling the electrographic onset of a seizure of claim 16 wherein the minimally required intervention measures starts with a benign form of therapy and continues with more aggressive therapies as the probability vector continuously changes with decreasing time to electrographic onset.

18. The system for automatically predicting and controlling the electrographic onset of a seizure of claim 16 wherein the minimally required intervention measures couples minimally invasive benign therapies to long prediction time intervals, aggressive therapies to short prediction time intervals and gradually varying moderate forms of therapy to prediction time intervals that are between the long and short prediction time intervals.

* * * * *